United States Patent
Chandrapati et al.

(10) Patent No.: US 10,640,743 B2
(45) Date of Patent: *May 5, 2020

(54) METHOD AND CULTURE DEVICE FOR DETECTING YEASTS AND MOLDS

(71) Applicant: 3M INNOVATIVE PROPERTIES COMPANY, St. Paul, MN (US)

(72) Inventors: Sailaja Chandrapati, Woodbury, MN (US); Tera M. Nordby, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/879,582

(22) Filed: Jan. 25, 2018

(65) Prior Publication Data

US 2018/0148675 A1    May 31, 2018

Related U.S. Application Data

(63) Continuation of application No. 14/813,897, filed on Jul. 30, 2015, now Pat. No. 9,879,214, which is a continuation of application No. PCT/US2014/041523, filed on Feb. 4, 2014, which is a continuation of application No. 13/775,495, filed on Feb. 25, 2013, now Pat. No. 8,921,067.

(60) Provisional application No. 61/760,412, filed on Feb. 4, 2013.

(51) Int. Cl.
| | |
|---|---|
| *C12Q 1/04* | (2006.01) |
| *C12M 1/00* | (2006.01) |
| *G01N 33/52* | (2006.01) |
| *C12M 1/12* | (2006.01) |
| *C12M 1/04* | (2006.01) |

(52) U.S. Cl.
CPC ............ *C12M 23/20* (2013.01); *C12M 23/04* (2013.01); *C12M 23/24* (2013.01); *C12Q 1/04* (2013.01); *G01N 33/52* (2013.01)

(58) Field of Classification Search
None
See application file for complete search history.

(56) References Cited

U.S. PATENT DOCUMENTS

| | | |
|---|---|---|
| 4,565,783 A | 1/1986 | Hansen et al. |
| 5,089,413 A | 2/1992 | Nelson et al. |
| 5,364,766 A | 11/1994 | Mach et al. |
| 5,448,652 A | 9/1995 | Vaidyanathan et al. |
| 5,601,998 A | 2/1997 | Mach et al. |
| 5,635,367 A | 6/1997 | Lund |
| 5,681,712 A | 10/1997 | Nelson |
| 5,739,429 A | 4/1998 | Schmitkons et al. |
| 5,854,011 A | 12/1998 | Chen et al. |
| 5,888,760 A | 3/1999 | Godsey et al. |
| 5,958,675 A | 9/1999 | Wicks et al. |
| 5,962,251 A | 10/1999 | Rambach |
| 6,046,016 A | 4/2000 | Orenga |
| 6,058,209 A | 5/2000 | Vaidyanathan et al. |
| 6,090,541 A | 7/2000 | Wicks et al. |
| 6,243,486 B1 | 6/2001 | Weiss |
| 6,271,022 B1 | 8/2001 | Bochner |
| 6,387,650 B1 | 5/2002 | Townsend et al. |
| 7,141,387 B2 | 11/2006 | Ushiyama |
| 7,298,885 B2 | 11/2007 | Green et al. |
| 7,319,031 B2 | 1/2008 | Vent et al. |
| 8,415,115 B2 * | 4/2013 | Orenga ............... C12Q 1/14 435/18 |
| 8,753,834 B2 * | 6/2014 | Miller ............... C12Q 1/04 435/34 |
| 8,921,067 B2 * | 12/2014 | Chandrapati ......... C12M 23/04 435/34 |
| 9,602,794 B2 | 3/2017 | Chang |
| 2005/0239200 A1 | 10/2005 | Beckwith |
| 2006/0008867 A1 | 1/2006 | Ushiyama |
| 2008/0259769 A1 | 10/2008 | Zhou |

FOREIGN PATENT DOCUMENTS

| | | |
|---|---|---|
| JP | H11-512935 | 11/1999 |
| JP | 2002-513288 | 5/2002 |
| JP | 03-015379 | 1/2003 |

(Continued)

OTHER PUBLICATIONS

US 4,476,226 A, 10/1984, Hansen et al. (withdrawn)
Bascomb, S. et al.; "Use of Enzyme Tests in Characterization and Identification of Aerobic and Facultatively Anaerobic Gram-Positive Cocci"; Clinical Microbiology Reviews; vol. 11, No. 2; 1998; pp. 318-340.
Slots, J.; "Enzymatic Characterization of Some Oral and Nonoral Gram-Negative Bacteria with the API ZYM System"; Journal of Clinical Microbiology; vol. 14, No. 3; 1981; pp. 288-294.

*Primary Examiner* — Vera Afremova

(74) *Attorney, Agent, or Firm* — Eric E. Silverman

(57) ABSTRACT

A thin film culture device for detecting yeast and mold microorganisms in a sample is provided. The culture device comprises a body comprising a self-supporting substrate having a first major surface and a second major surface; a first adhesive composition disposed on a portion of the first major surface of the substrate; a substantially dry, cold-water-soluble first hydrogel-forming composition adhered to the first adhesive composition; and a plurality of indicator agents. The plurality of indicator agents comprises three indicator agents for detecting distinct glycosidase enzyme activities, an indicator agent for detecting an alkyl esterase enzyme activity, and an indicator agent for detecting a phosphatase enzyme activity, wherein each of the plurality of indicator agents comprises a detectable reporter group. A method of using the culture device is also provided.

11 Claims, 1 Drawing Sheet

(56) References Cited

FOREIGN PATENT DOCUMENTS

| WO | WO 1998/45469 | 10/1998 |
| WO | WO 2011/082305 | 7/2011 |
| WO | WO 2014/121243 | 8/2015 |

\* cited by examiner

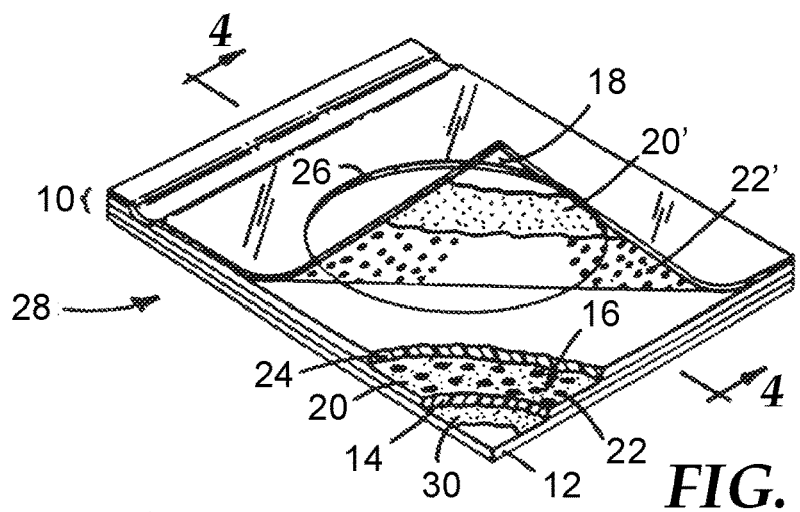
FIG. 2
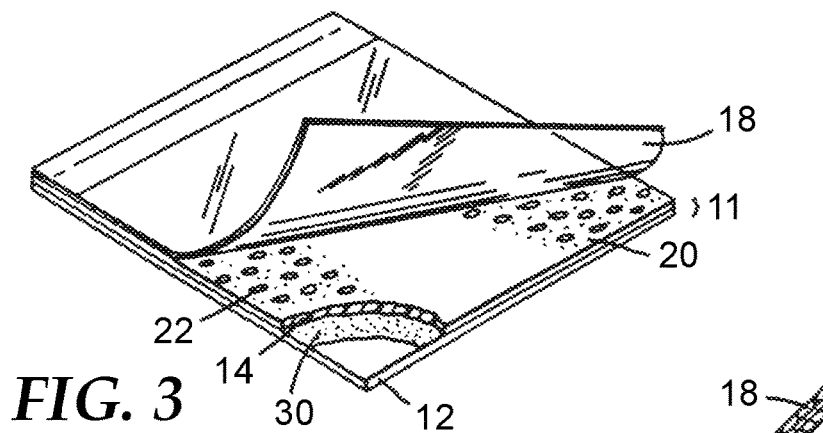
FIG. 3
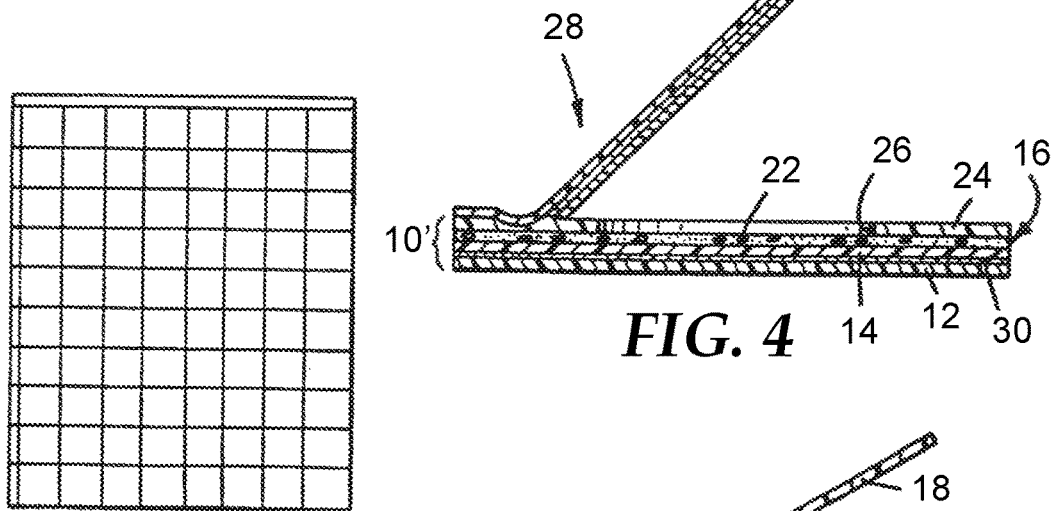
FIG. 4
FIG. 5
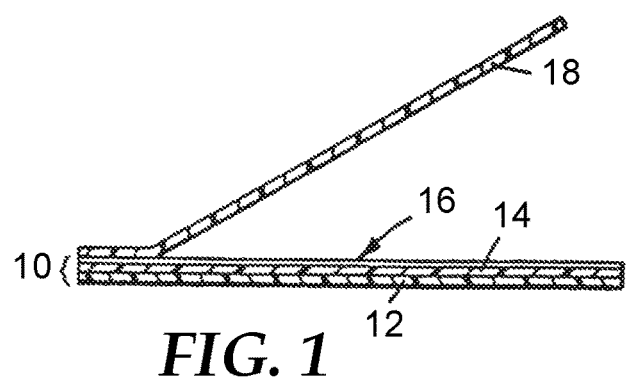
FIG. 1

METHOD AND CULTURE DEVICE FOR DETECTING YEASTS AND MOLDS

CROSS REFERENCE TO RELATED APPLICATION

This application is a continuation of U.S. patent application Ser. No. 14/813,897, filed Jul. 30, 2015, now U.S. Pat. No. 9,879,214, which is a continuation of PCT/US2014/014523, filed Feb. 4, 2014, which claims the benefit of U.S. patent application Ser. No. 13/775,495, filed Feb. 25, 2013, now U.S. Pat. No. 8,921,067 and U.S. Provisional Patent Application No. 61/760,412, filed Feb. 4, 2013, the disclosures of which are incorporated by reference in their entirety herein.

BACKGROUND

Yeasts and molds are eukaryotic microorganisms. They are ubiquitous in natural environments, namely, soil, air, water, and plant surfaces. Because of their heterotrophic nature and their ability to adapt to a wide range of environmental conditions, these microbes are frequently encountered as an expensive nuisance in and on various commodities including food ingredients, processed foods, beverages, inadequately cleaned food processing equipment, and food storage facilities. In addition, some yeasts and molds possess potential hazard to human and animal health. For example, numerous molds produce mycotoxins and some yeasts and molds are responsible for human and animal infections.

Yeast or mold contamination in food and other commodities can result in substantial economic losses for the producer, the processor, and the consumer. Rapid and accurate determinations of yeast and/or mold contamination in a commodity (such as, food ingredients, processed foods, and beverages), are important for the production of high-quality food products in the food industry.

Current practices for routine determination of yeasts and molds in a food commodity rely largely on conventional culturing techniques for enumerating viable fungal cells on semi-solid agar media. These methods, although widely accepted, have a number of disadvantages in that they are, in general, labor intensive and give low reproducibility. In addition, a common problem encountered in the traditional methods is that the spreading type of mycelial growth of certain molds often over-runs nearby colonies and prevents accurate enumeration of the viable cells in a sample.

Most importantly, most of these methods require a 5 day incubation period at 25° C. before accurate quantitative results can be obtained. The long incubation period of these methods can require that food products be stored for several days, until the presence or concentration of contaminating yeasts and/or molds is finally known. Thus, there is a need for improved tests and related materials. If the test procedures could be simplified, and test results obtained in a shorter period of time, it would allow manufacturers to release products; thereby reducing storage costs without sacrificing product quality and integrity.

SUMMARY

The present disclosure generally relates to a culture device and method for the detection of yeast or mold microorganisms in a sample. In particular, the present disclosure relates to rapid detection of yeast and mold microorganisms in a dry, reconstitutable culture device comprising a plurality of indicator agents disposed at high concentrations in an adhesive composition. The plurality of indicator agents includes an indicator agent for detecting an alkyl esterase enzyme activity, an indicator agent for detecting a phosphatase enzyme activity, and three indicator agents for detecting distinct glycosidase enzyme activities. Advantageously, the plurality of indicator agents permits detection and enumeration of a wide variety of slow-growing yeast and mold microorganisms. Even more advantageously, the specific indicator agents, together with the concentrations thereof and the means for providing the indicator agents to the microorganisms, permit the detection and enumeration of the yeast and mold microorganisms in less than 120 hours and, preferably, in less than 72 hours. In any embodiment, the culture device may comprise malt extract. Advantageously, the malt extract acts cooperatively with the plurality of indicators to provide faster detection of yeast and/or mold colonies than otherwise possible.

In one aspect, the present disclosure provides a culture device. The culture device can comprise a body comprising a self-supporting substrate having a first major surface and a second major surface, a first adhesive composition disposed on a portion of the first major surface of the substrate, a substantially dry, cold-water-soluble first hydrogel-forming composition adhered to the first adhesive composition, and a plurality of indicator agents. The plurality of indicator agents comprises three indicator agents for detecting distinct glycosidase enzyme activities, an indicator agent for detecting an alkyl esterase enzyme activity, and an indicator agent for detecting a phosphatase enzyme activity, wherein each of the plurality of indicator agents comprises a detectable reporter group. In any embodiment, the culture device further can comprise a coversheet attached to the body member.

In any of the above embodiments, the culture device further can comprise a cover sheet attached to the body member. In any embodiment, the cover sheet can comprise a first major surface facing the body member; wherein the culture device further can comprise a second adhesive composition disposed on a portion of the first major surface of the cover sheet and a substantially dry, cold-water-soluble second hydrogel-forming composition adhered to the second adhesive composition. In any of the above embodiments, the at least three indicator agents for detecting distinct glycosidase enzyme activities can include a compound to detect alpha-glucosidase enzyme activity, a compound to beta-glucosidase enzyme activity, and a compound to beta-galactosidase enzyme activity. In any of the above embodiments, the at least one nutrient can comprise malt extract. In any of the above embodiments, the culture device further can comprise a water-insoluble spacer having an aperture, the spacer being attached to the body member or the coversheet and the entire aperture being positioned between the body member and the cover sheet. In any of the above embodiments, at least one of the plurality of indicator agents can be disposed in the first adhesive composition, the second adhesive composition, the first hydrogel-forming composition, and/or the second hydrogel-forming composition. In any of the above embodiments, the first hydrogel-forming composition or the second hydrogel-forming composition can comprise at least one nutrient for growing yeast or mold microorganisms.

In another aspect, the present disclosure provides a method of detecting yeast and mold in a sample. The method can comprise contacting a sample and an aqueous liquid with a gelling agent of a culture device to form an inoculated culture device, incubating the inoculated culture device for a period of time, and detecting a yeast or mold colony in the culture device. The culture device comprises a self-supporting substrate having a first major surface and a second major surface, a first adhesive composition disposed on a portion of the first major surface of the substrate, a cold-water-soluble first hydrogel-forming composition adhered to the first adhesive composition, and the plurality of indicator agents. The plurality of indicator agents comprises three indicator agents for detecting distinct glycosidase enzyme activities, an indicator agent for detecting an alkyl esterase enzyme activity, and an indicator agent for detecting a phosphatase enzyme activity, wherein each of the plurality of indicator agents comprises the detectable reporter group. Optionally, the culture device comprises a coversheet that includes a second adhesive composition disposed thereon and a cold-water-soluble second hydrogel-forming composition adhered to the second adhesive composition. The first hydrogel-forming composition or the second hydrogel-forming composition, if present, comprises the gelling agent and, optionally, at least one nutrient for growing yeast or mold microorganisms. Each of the plurality of indicator agents is disposed in the first adhesive composition, the second adhesive composition, the first hydrogel-forming composition, or the second hydrogel-forming composition. In any embodiment, the method further can comprise enumerating yeast or mold colonies present in the inoculated culture device after incubating the inoculated culture device. In any embodiment, detecting a yeast or mold colony in the culture device can comprise detecting in the culture device a presence or an absence of a detectable reporter group of at least one of a plurality of indicator agents, wherein detecting the presence of the detectable reporter group is indicative of a presence of a colony of yeast or mold microorganisms.

The term "powder", as used herein, refers to particulate material of one or more gelling agents or nutrients having an average diameter suitable for use in the thin film culture device(s) of the present invention, preferably a diameter of about 10-400 microns more preferably a diameter of about 30-90 microns.

As used herein, "reconstituted medium" refers to a solution or gel formed from the reconstitution of a cold-water-soluble powder with an aqueous liquid.

The term "cold-water-soluble powder", as used herein, refers to a powder that forms a gel in room temperature water (e.g., about 18° C. to 24° C.) when combined with an aqueous test sample.

The term "substantially impermeable to microorganisms and water vapor", as used herein, refers to a cover sheet that prevents undesired contamination and hydration of underlying layers of cold-water-soluble powder during shipping, storage, and use of thin film culture device(s), and avoids desiccation of the reconstituted medium, such that the reconstituted medium is suitable to support the growth of microorganisms during an incubation period.

As used herein, "selective agent" refers to any element, compound, or composition that functions to inhibit the growth of one type of microorganism (e.g., a bacterium) relative to another type of microorganism (e.g., a yeast or a mold) and thereby facilitate the growth and/or identification of microorganisms grown on the thin film culture device(s) according to the present disclosure.

The term "yeast", as used herein, refers to a typically-unicellular fungus of the phylum Ascomycota that reproduces asexually by fission and/or budding. Yeast includes one or more species existing or co-existing collectively in a test sample. The term "yeasts" also refers to the array of yeasts found, e.g., in a test sample. The terms "yeast" or "yeasts" are not limited to mean any given number of these species and are not meant to exclude species which have yet to be discovered but may later be identified and included in this definition by those of skill in the art.

The term "mold", as used herein refers to a microscopic fungus. This term is not limited to mean any given number of these species and is not meant to exclude species which have yet to be discovered but may later be identified and included in this genus by those of skill in the art.

The term "test sample", as used herein, refers to a component or portion taken from a food product, a human or animal test subject, pharmaceutical or cosmetic commodity, soil, water, air or other environmental source, or any other source from which a yeast and mold concentration is to be determined. A test sample may be taken from a source using techniques known to one skilled in the art including, for example, pouring, pipetting, swabbing, filtering, and contacting. In addition, the test sample may be subjected to various sample preparation processes known in the art including, for example, blending, stomaching, homogenization, enrichment, selective enrichment, or dilution.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a culture device comprising "an" indicator agent can be interpreted to mean that the culture device can comprise "one or more" indicator agents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The figures and the detailed description which follow more particularly exemplify illustrative embodiments. Other features, objects and advantages will become apparent from the description and drawings, and from the claims.

BRIEF DESCRIPTION OF DRAWINGS

FIG. 1 is a cross-sectional view of a device of the present disclosure, wherein certain features are shown.

FIG. 2 is a top perspective view, partially in section, of one embodiment of a culture device according to the present disclosure.

FIG. 3 is a top perspective view of an alternative embodiment of a culture device according to the present disclosure.

FIG. 4 is a cross sectional view of culture device of FIG. 2 taken along line 4-4.

FIG. 5 is a top view of the culture device of FIG. 2 showing a grid pattern printed on the microporous membrane.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

Yeasts and molds are ubiquitous eukaryotic microorganisms that remain viable in certain (e.g., low water activity, low pH) environments that are detrimental to most other unicellular microorganisms. Classified as food spoilage indicator organisms, tests for yeasts and molds constitute about 14% of all routinely conducted indicator-organism testing because yeast and mold microorganisms are frequently encountered as an expensive nuisance in and on various commodities (e.g., food ingredients, processed foods, beverages), inadequately cleaned food processing equipment, and food storage facilities. In addition, some yeasts and molds have clinical relevance as causative agents of human and animal infections.

Traditional testing for yeast and molds typically involve culturing the microorganisms on agar media or in thin-film culture devices such as a 3M PETRIFILM Yeast & Mold Count Plate (available from 3M Company, St. Paul, Minn.). Thin film culture devices for detecting yeast and mold in a sample are described, for example, in U.S. Pat. No. 5,089,413, which is incorporated herein by reference in its entirety. The traditional testing methods involve incubating the test plates for a period of up to 5-7 days to get accurate counts. This relatively lengthy time to result can cause food manufacturers to hold the food product prior for up to seven days in order to determine whether the food product contains a yeast or mold microorganism that may adversely affect the quality and/or safety of the food product during normal conditions of storage.

Some culture media, including the culture medium used in 3M PETRIFILM Yeast & Mold Count plates, include at least one indicator reagent (e.g., 5-bromo-4-chloro-3-indolylphosphate sodium salt) that is converted by yeast or mold microorganisms to a detectable (e.g., detectable by light absorption, reflectance, and/or fluorescence) product. U.S. Pat. No. 6,387,650; which is incorporated herein by reference in its entirety; discloses compositions for detecting yeast and fungi in a test sample, wherein the compositions comprise three enzyme substrates that cause or produce an identical type of detectable signal (e.g., fluorescence) when hydrolyzed by a corresponding enzyme activity found in the microorganisms. One enzyme substrate is hydrolyzed by a glycosidase enzyme activity, a second enzyme substrate is hydrolyzed by a peptidase enzyme activity and the third enzyme substrate is hydrolyzed by a phosphatase enzyme activity. In the patent, Townsend and Chen further describe the use of media containing the indicator reagents in a culture device that permits the calculation of a most probable number (MPN) of microorganisms in the test sample.

Chen and Gu (U.S. Pat. No. 5,854,011; which is incorporated herein by reference in its entirety) describe a method and compositions for detecting yeast and/or molds in a sample wherein the composition includes an aminopeptidase enzyme substrate and an inhibitor of aminopeptidase enzyme activity in an amount effective to inhibit aminopeptidase activity that is endogenous to the test sample. In Example 1, Chen and Gu conclude that, because they were found in ≤64% of the microorganisms tested, phosphatase, β-glucosidase, and α-glucosidase enzymes are unsuitable to be used as the target enzyme for detecting total yeasts and molds in a sample.

As evidenced by Chen and Gu, it is difficult to find an enzyme substrate that can detect the wide variety of yeasts and molds that are found in nature. The inventive article and method of the present disclosure provide detection of a variety of yeast and mold. In addition, the inventive article and method can provide rapid detection of the yeast and mold microorganisms. In some embodiments, the investigators have discovered a composition comprising a unique combination of indicators in a nutrient medium comprising malt extract. In a culture device of the present disclosure, the composition is suitable for the rapid detection of a variety of yeast and mold microorganisms.

In one aspect, the present disclosure provides a culture device for detecting yeast and mold microorganisms in a sample. The components of the culture device, when contacted with an aqueous liquid, can act cooperatively to form an aqueous culture medium that is used to cultivate yeast and mold (e.g., filamentous fungi) microorganisms. In any embodiment, the culture medium of the present disclosure can be a mixture which comprises all or substantially all of the nutrients necessary to support the growth of yeasts and molds. In some embodiments, one or more nutrients to support the growth of yeast and mold microorganisms may be provided in the sample.

The culture device of the present disclosure provides improved detection (i.e., reduced time to detection, more inclusive detection of yeast and mold microorganisms within a specified incubation period) compared to other devices and methods known in the art. In some aspects, a culture device of the present disclosure is related to thin film culture devices disclosed in U.S. Pat. Nos. 4,565,783; 5,089,413; and 5,681,712; which are all incorporated herein by reference in their entirety.

Suitable samples for use with the inventive culture device can be obtained or derived from a variety of sources. The term "source" is generally used to refer to the food or nonfood desired to be tested for microorganisms. The source can be a solid, a liquid, a semi-solid, a gelatinous material, gas (e.g., air), and combinations thereof. In some embodiments, the source can be provided by a capture element (e.g., a filter membrane, swab, fabric, or sponge) that was used, for example, to collect the source from a surface of interest or from air. In some embodiments, a sample liquid can include the capture element, which can be further broken apart (e.g., during an agitation or dissolution process) to enhance retrieval of the source and any microorganism of interest. The surface of interest can include at least a portion of a variety of surfaces, including, but not limited to, walls (including doors), floors, ceilings, drains, refrigeration systems, ducts (e.g., air ducts), vents, toilet seats, handles, doorknobs, handrails, countertops, tabletops, eating surfaces (e.g., trays, dishes, etc.), working surfaces, equipment surfaces, clothing, etc., and combinations thereof. All or a portion of the source can be used in the method. When a portion of the source is used, this can sometimes be referred to as a "sample" of the source. However, the term "sample" is generally used herein to refer to the portion of volume or mass of material that is obtained from the source and is introduced into a test device for the detection of microorganisms.

The term "food" is generally used to refer to a solid, liquid (e.g., including, but not limited to, solutions, dispersions, emulsions, suspensions, etc., and combinations thereof) and/or semi-solid comestible composition. Examples of foods include, but are not limited to, meats, poultry, eggs, fish, seafood, vegetables, fruits, prepared foods (e.g., soups, sauces, pastes), grain products (e.g., flour, cereals, breads), canned foods, milk, other dairy products (e.g., cheese, yogurt, sour cream), fats, oils, desserts, condiments, spices, pastas, beverages, water, animal feed, other suitable comestible materials, and combinations thereof.

With reference to FIG. 1, a device of the present disclosure is shown as body member 10 with three salient features: waterproof substrate 12, air-permeable membrane 14, and substantially dry, cold-water-soluble first hydrogel-forming composition 22. Although these can be arranged in any suitable relationship, FIG. 1 illustrates a preferred arrangement of these components, wherein air permeable membrane 14 is fixed to and covers at least the growth region (not shown) of the top surface of substrate 12. First hydrogel-forming composition 22 is fixed to and covers at least the growth region of the top surface of membrane 14. Cover means (coversheet 18) for covering the first hydrogel-forming composition 22 during shipping, storage, and incubation, is also shown in FIG. 1 as being attached in a hinge-like fashion along one edge of body member 10. Cover means are optional but preferred in devices of the present disclosure. Suitable substrates, first hydrogel-forming composition and cover means include those described in U.S. Pat. No. 4,565,783, which is incorporated herein by reference in its entirety.

Substrate 12 can be a relatively stiff film (e.g., polyester, polypropylene or polystyrene) or a relatively stiff paper or cardboard having a water-resistant coating thereon, which will not absorb or otherwise be affected by water. Polyester films approximately 100μ to 180μ, thick, polypropylene films approximately 100μ to 200μ thick, and polystyrene films approximately 300μ to 380μ thick are nonlimiting examples of suitable materials for the substrate 12. The substrate 12 may be either transparent or opaque, depending on whether one wishes to view microorganism colonies through the substrate. To facilitate the counting of microorganism colonies, the substrate 12 optionally can have a grid pattern (e.g., squares, not shown) printed thereon.

Air-permeable membrane 14 allows an adequate supply of air to first hydrogel-forming composition 22 when coversheet 18 is in place after the device is inoculated. In so doing, membrane 14 is useful for supporting growth of aerobic microorganisms in the device. By virtue of the air permeability of the membrane and the membrane being substantially exposed at its edge(s) to air, air is able to pass into the edge(s) of the membrane, horizontally through the membrane, and into the medium. Horizontal passage of air for a particular membrane is most conveniently estimated by evaluating the vertical air permeability of the membrane (i.e., permeability in a direction normal to the top and bottom surfaces of the membrane). Suitable air permeable membrane 14 materials, including microporous films and microporous non-woven webs of synthetic or natural materials, are described in U.S. Pat. No. 5,089,413, which is incorporated herein by reference in its entirety. A nonlimiting example of a preferred membrane material is a microporous polyolefin film (TREDEGAR EXXAIRE film, Tredegar Film Products, Richmond, Va.).

In any embodiment, the membrane 14 has a visible square grid pattern printed upon it, as shown in FIG. 5, to facilitate the counting of microorganism colonies. A device of the present disclosure can be prepared using a variety of techniques. Generally, a device can be made by hand or with common laboratory equipment as described in detail below.

FIGS. 2 and 4 illustrate a device in accordance with the present disclosure. Device 28 includes a body member 10' having a water-proof substrate 12 with a top surface and a bottom surface. The bottom surface of membrane 14 is fixed to (e.g., fixed with an adhesive or otherwise attached to) at least the growth region (not shown) of the top surface of substrate 12. Preferably, the top surface of substrate 12 is coated with adhesive layer 30, which is used to fix membrane 14. Adhesive layer 30 is preferably pressure-sensitive, insoluble in water, and substantially non-inhibitory to the growth of the intended microorganisms, as described herein. Preferred adhesives include those discussed below in connection with first adhesive composition 20 and second adhesive composition 20'. Often, suitable substrates are available already coated with a suitable adhesive. If one desires, however, a suitable substrate can be selected and coated (e.g., using a knife coater) with a suitable adhesive.

The method of fixing membrane 14 to substrate 12 will depend on the nature of adhesive layer 30. If adhesive layer 30 is pressure sensitive for instance, membrane 14 can be placed on adhesive layer 30, pressed down, and thereby adhered in place.

Referring to FIGS. 2 and 3, substrate 12 is coated on a portion of its first surface with a layer of first adhesive composition 20. In any embodiment, the first adhesive composition 20 may comprise one or more indicator agents (not shown) and/or one or more selective agents (not shown) as described herein. Adhered to the first adhesive composition 20 is a substantially dry, cold-water-soluble first hydrogel-forming composition 22 which, optionally, includes a powdered nutrient 16. Thus, the thickness of the first adhesive composition 20 preferably should be less than the diameter of the particles of the powdered gelling agent and/or nutrients that make up the cold-water-soluble first hydrogel-forming composition 22. A uniform monolayer of cold-water-soluble first hydrogel-forming composition 22 is desired with sufficient surface area exposed for hydration.

An adhered powder medium, illustrated in FIGS. 2 and 3, is prepared and fixed by first forming a layer of first adhesive composition 20 on at least the growth region of the top surface of membrane 14. The adhesive of the first adhesive composition 20 is preferably pressure-sensitive, insoluble in water, and substantially non-inhibitory to the growth of the intended microorganisms. Preferably, first adhesive composition 20 is also sufficiently transparent when wet to enable viewing of microbial colonies.

Attached to the substrate 12 is optional coversheet 18. In any embodiment, cover sheet 18 can be affixed to one edge of substrate 12 (e.g., via heat sealing or a double-sided tape).

Cover sheet 18 is translucent or preferably transparent to facilitate counting of the microorganism colonies, and is substantially impermeable to both microorganisms and water vapor. Generally, cover sheet 18 will have the same properties, such as transparency and preferred water impermeability, as substrate 12. Furthermore, cover sheet 18 can have patterns imprinted thereon, such as square grid pattern, or a mask-edge (not shown) to aid in the counting of microorganism colonies, to provide a target for placement of the aqueous test sample, and/or for aesthetic reasons. Cover sheet 18 can be selected to provide an amount of oxygen transmission necessary for yeast and mold microorganisms, some of which require relatively oxygen-rich environments for optimal growth conditions. Suitable cover sheet materials are disclosed in U.S. Pat. No. 5,681,712.

Cover means (e.g., coversheet 18) can be free of any coating, or can be coated, e.g., on the surface facing the dry medium with a layer of pressure-sensitive adhesive, in order to facilitate sealing of the cover means over the medium. Furthermore, coversheet 18 can optionally be coated on the surface facing the first hydrogel-forming composition 22 with layers of second adhesive composition 20' and second hydrogel-forming composition 22', that are the same as or different from first adhesive composition 20 and first hydrogel-forming composition 22, respectively. Coatings on coversheet 18 can cover the entire surface facing the first hydrogel-forming composition 22, but preferably cover at least the part of the surface that is intended to cover the growth region of the culture device. Such coated coversheets are particularly preferred when it is desired to provide a device with more gelling agent than can be incorporated in the first hydrogel-forming composition alone.

Coversheet 18 is preferably adhered in a hinge-like fashion along one edge of spacer 24, and is optionally coated with a layer of second adhesive composition 20' and second hydrogel-forming composition 22'. In any embodiment, the second adhesive composition can comprise one or more (e.g., all) of the plurality of indicator agents used to detect yeast and/or mold microorganisms. Alternatively, coversheet 18 can be adhered directly to the substrate 12 as illustrated in FIG. 3.

If a culture device (not shown) of the present disclosure does not include a coversheet attached to the substrate, the culture device should be stored and incubated in a container (e.g., a petri dish) in order to prevent contamination and/or desiccation of the device and sample before and after inoculation.

Also shown in FIG. 2 is an optional second adhesive composition 20' disposed on at least a portion of coversheet 18; a substantially dry, cold-water-soluble second hydrogel-forming composition 22' disposed on second adhesive composition 20'; and an optional spacer 24. When hydrated with an aqueous liquid (e.g., a liquid sample and/or an aqueous suspending medium, such as water or a buffer), a gelling agent present in the first hydrogel-forming composition 22 and/or second hydrogel-forming composition 22' forms a hydrogel.

As depicted in FIGS. 2 and 4, the culture device can include a spacer 24 attached (e.g., via heat bonding or a pressure-sensitive adhesive) to a first surface of substrate 12, the first adhesive composition 20, and/or the first hydrogel-forming composition 22. The spacer 24 comprises an aperture (e.g., circular aperture 26) cut through the center to expose the first hydrogel-forming composition 22. The walls of aperture 26 provide a well of predetermined size and shape to confine the hydrogel following hydration of the first hydrogel-forming composition 22 with an aqueous liquid.

The aperture 26 generally delineates a growth area of the culture device. Spacer 24 should be thick enough to form a well of the desired volume, e.g., 1, 2 or 3 milliliters. Closed cell polyethylene foam is a preferred material for spacer 24, but any material which is hydrophobic (non-wetting), inert to microorganisms, and capable of withstanding sterilization may be used. In some embodiments (not shown), the spacer can comprise a plurality of apertures (e.g., 2, 3, 4, 5, 6, 7, 8, 9, 10, 12, 15, or 20 apertures), each of which can be inoculated with a distinct sample.

Suitable materials for the spacer member are any solid non-inhibitory natural or synthetic substance which is readily available in sheet form but is not a microorganism growth site. Polyethylene, polypropylene, polyethylene terephthalate and polystyrene are a few examples of suitable synthetic materials. In particular, relatively inexpensive commercially available polystyrene foams and polyethylene foams are preferred.

Spacer 24 can include relatively thick designs, such as those described in U.S. Pat. No. 5,681,712. One purpose of the thicker (e.g., at least about 0.5 mm thick, about 1 mm thick, about 1.5 mm thick and about 2 mm thick) apertured spacer 24 is to locate and protect membranes (e.g. microporous filter membranes, not shown) placed in the aperture 26 of the spacer 24. Another purpose of the thicker spacer 24 is to reduce or prevent contact by cover sheet 18 with the growing colonies of microorganisms (i.e., provide a "head space" between the growth surface and the cover sheet 18, which can also provide increased aeration for growing colonies of microorganisms).

The first adhesive composition 20 and, if present, second adhesive composition 20' preferably is a pressure sensitive adhesive. More preferably, the adhesive is a pressure-sensitive adhesive such as a water-insoluble adhesive comprising a copolymer of an alkyl acrylate monomer and an alkyl amide monomer. Preferably the weight ratio of alkyl acrylate monomer to alkyl amide monomer in these copolymers is from about 90:10 to 99:1, more preferably 94:6 to 98:2. The alkyl acrylate monomer comprises a lower alkyl (C2 to C10) monomer of acrylic acid, including, for example, isooctyl acrylate (IOA), 2-ethylhexyl acrylate, butyl acrylate, ethyl acrylate, isoamyl acrylate, and mixtures thereof, while the alkyl amide monomer can comprise, without limitation, acrylamide (ACM), methacrylamide, N-vinylpyrrolidone (NVP), N-vinylcaprolactam (NVCL), N-vinyl-2-piperidine, N-(mono- or di-lower alkyl (C2 to C5))(meth)acrylamides, N-methyl(meth)acrylamide, N,N-dimethyl(meth) acrylamides, or mixtures thereof.

In any embodiment, the first adhesive composition 20 and/or second adhesive composition 20' may comprise an indicator agent (not shown) and/or selective agent. In any embodiment, the indicator agent may be dissolved in an organic solvent (e.g., methanol) and blended with the adhesive composition before applying the composition to the substrate 12 and/or coversheet 18. In any embodiment, the first adhesive composition 20 and/or second adhesive composition 20' may include a plurality of indicator agents. In any embodiment the first adhesive composition 20 and second adhesive composition 20' each may include an identical indicator agent. In any embodiment the first adhesive composition 20 and second adhesive composition 20' each may include an indicator agent or selective that is not included in the other adhesive composition.

In any embodiment, one or more indicator agent of the present disclosure can be disposed as a powder (or an agglomerated powder) in the first hydrogel-forming composition 22 and/or second hydrogel-forming composition 22' disclosed herein.

In any embodiment, a culture device of the present disclosure comprises a plurality of indicator agents (e.g., enzyme substrates), each indicator agent comprising a reporter group (e.g., a fluorogenic group or chromogenic group) that permits detection of a reaction between the indicator agent and a biological activity (i.e., an enzyme activity associated with a yeast or mold microorganisms) and the indicator agent. In any embodiment, the plurality of indicator agents can comprise five indicator agents. In any embodiment, the five indicator agents can include three agents for detecting three distinct glycosidase enzyme activities, an indicator agent for detecting an esterase enzyme activity (e.g., an alkyl esterase enzyme activity), and an indicator agent for detecting a phosphatase enzyme activity. The culture medium further comprises a gelling agent. In any embodiment, the plurality of indicator agents does not include an indicator agent for detecting aminopeptidase enzyme activity.

Yeast and mold microorganisms produce one or more of a variety of glycosidase enzyme activities, each glycosidase enzyme activity being capable of reacting with an indicator reagent to produce a detectable product. Tables 1 and 2 list nonlimiting examples of indicator agents that may react with a corresponding enzyme activity, if present, within or proximate a colony of yeast or mold microorganisms.

TABLE 1

Indicator agents for detecting glycosidase enzyme activities.

| | | |
|---|---|---|
| 4-Methylumbelliferyl-N-acetate-β-D-galactosaminide | 4-Methylumbelliferyl-β-D-xylose | 4-Nitrophenyl-β-D-fucopyranoside |
| 4-Methylumbelliferyl-N-acetate-β-D-glucosaminide | 6-Bromo-2-naphthyl-N-acetyl-β-D-glucosaminide | 2-Nitrophenyl-β-D-thiogalactopyranoside |
| 2'-(4-Methylumbellifelyl-α-D-N-acetyl-neuraminic acid Sodium salt | 6-Bromo-2-naphthyl-α-D-glucopyranoside | Phenolphthalein-mono-β-D-galactopyranoside |
| 4-Methylumbelliferyl-α-L-arabinopyranoside | 6-Bromo-2-naphthyl-β-D-xylopyranoside | 5-Bromo-4-chloro-3-Indolyl-N-acetyl-β-D-galactosaminide |
| 4-Methylumbelliferyl-β-D-cellobiopyranoside | Naphthol AS-BI-β-L-fucopyranoside | 5-Bromo-4-chloro-3-Indolyl-β-D-fucopyranoside |
| 4-Methylumbelliferyl-β-D-fucoside | 1-Naphthyl-α-D-galactopyranoside | Indoxyl-β-D-galactoside |
| 4-Methylumbelliferyl-α-D-mannoside | 2-Nitrophenyl-N-acetyl-α-D-galactosaminide | 4-Nitrophenyl-α-L-fucopyranoside |
| 4-Methylumbelliferyl-6-sulfo-N-acetyl-β-D-glucosaminide | 4-Nitrophenyl-β-D-cellobioside | 4-Nitrophenyl-β-L-fucopyranoside |
| 4-Methylumbelliferyl-β-D-cellotriose | 6-Bromo-2-naphthyl-β-D-galactoside | 2-Nitrophenyl-α-D-galactopyranoside |
| 4-Methylumbelliferyl-β-D-N,N'-diacetyl-chitobioside | 6-Bromo-2-naphthyl-β-D-glucopyranoside | 2-Nitrophenyl-β-D-galactopyranoside |
| 4-Methylumbelliferyl-α-L-fucoside | 6-Bromo-2-naphthyl-β-D-glucuronide | 3-Nitrophenyl-α-D-galactopyranoside |
| 4-Methylumbelliferyl-β-L-fucoside | 2-Chloro-4-nitrophenyl-N-acetyl-β-D-glucosaminide | 3-Nitrophenyl-β-D-galactopyranoside |
| 4-Methylumbelliferyl-α-D-galactoside | 2-Chloro-4-nitrophenyl-β-D-cellobioside | 4-Nitrophenyl-α-D-galactopyranoside |
| 4-Methylumbelliferyl-β-D-galactoside | 2-Chloro-4-nitrophenyl-β-D-xylopyranoside | 4-Nitrophenyl-β-D-galactopyranoside |
| 4-Methylumbelliferyl-β-D-galactoside-6-phosphate Ammonium salt | β-Hydroxyquinoline-β-D-glucuronide | 4-Nitrophenyl-β-D-glucuronide |
| 4-Methylumbelliferyl-α-D-glucoside | Naphthol AS--BI-β-D-galactopyranoside | 4-Nitrophenyl-α-D-glucopyranoside |
| 4-Methylumbelliferyl-β-D-glucoside | Naphthol AS--BI-β-D-galactosaminide | 4-Nitrophenyl-β-D-glucopyranoside |
| 4-Methylumbelliferyl-β-D-glucuronide | Naphthol AS--BI-glucopyranoside | 4-Nitrophenyl-β-D-glucuronide |
| 4-Methylumbelliferyl-β-D-N,N',N'-triacetylchitotriose | Naphthol AS--BI-β-D-glucuronic acid | 2-Nitrophenyl-β-D-glucuronide |
| 5-Bromo-4-chloro-3-Indolyl-α-D-galactopyranoside | 1-Naphthyl-β-D-galactopyranoside | 4-Nitrophenyl-β-D-glucuronide |
| 4-Nitrophenyl-N-acetyl-1-thio-β-D-glucosaminide | 2-Naphthyl-β-D-galactopyranoside | 4-Nitrophenyl-β-D-thiogalactopyranoside |
| 4-Nitrophenyl-α-L-arabinopyranoside | 1-Naphthyl-β-D-glucuronide | 4-Nitrophenyl-β-D-thioglucopyranoside |
| 3-Nitrophenyl-β-D-fucopyranoside | 4-Nitrophenyl-N-acetyl-α-D-galactosaminide | Phenolphthalein-β-D-glucuronic acid Sodium salt |
| 4-Nitrophenyl-α-D-fucopyranoside | 4-Nitrophenyl-N-acetyl-β-D-galactosaminide | Phenyl-N-acetyl-α-D-glucosaminide |
| 5-Bromo-4-chloro-3-Indolyl-β-D-glucopyranoside | 4-Nitrophenyl-N-acetyl-α-D-glucosaminide | Phenylethyl-β-D-galactoside |
| 5-Bromo-4-chloro-3-Indolyl-β-D-glucuronic acid Cyclohexylammonium salt | 4-Nitrophenyl-N-acetyl-β-D-glucosaminide | Phenyl-β-D-galactoside |
| 5-Bromo-4-chloro-3-Indolyl-β-D-glucuronic acid Sodium salt | Indoxyl-β-D-glucoside | Phenyl-α-D-glucoside |
| 5-Bromo-4-chloro-3-Indolyl-α-D-mannopyranoside | Indoxyl-β-D-glucuronic acid Cyclohexylammonium salt | 5-Bromo-4-chloro-3-Indolyl-N-acetyl-β-D-glucosaminide |
| ALDOL 467 β-D- | ALDOL 470 α-D- | ALDOL 470 β-D- |

TABLE 1-continued

Indicator agents for detecting glycosidase enzyme activities.

| glucosaminide | glucopyranoside | galactopyranoside |
| ALDOL 518 β-D-galactopyranoside | ALDOL 467 β-D-galactopyranoside | ALDOL 458 β-D-galactopyranoside |

Yeast and mold microorganisms produce a variety of esterase enzyme activities including, for example, alkyl esterase (e.g., fatty acid alkyl esterase) enzyme activities and phosphatase (e.g., phosphoric monoester hydrolase) enzyme activities. Table 2 lists nonlimiting examples of indicator agents that may react with a corresponding esterase enzyme activity, if present, within or proximate a colony of yeast or mold microorganisms.

TABLE 2

Indicator agents for detecting alkyl esterase phosphatase enzyme activities.

| Alkyl esterase enzyme substrates | Phosphatase enzyme substrates |
|---|---|
| 4-Methylumbelliferyl-acetate | Bis(4-methylumbellifelyl)-phosphate |
| 4-Methylumbelliferyl-butyrate | Bis(4-methylumbellifelyl)-phosphate Sodium salt |
| 4-Methylumbelliferyl-laurate | 4-Methylumbelliferyl-phosphate (free acid) |
| 4-Methylumbelliferyl-nonaoate | 4-Methylumbelliferyl-phosphate Dicyclohexylammonium salt |
| 4-Methylumbelliferyl-oleate | 4-Methylumbelliferyl-phophate Disodium salt |
| 4-Methylumbelliferyl-palmitate | Bis(4-nitrophenyl)phosphate Sodium salt |
| 4-Methylumbelliferyl-propionate | Naphthol AS-phosphate |
| 4-Methylumbelliferyl-stearate | Naphthol AS-phosphate Sodium salt |
| 6-Bromo-2-naphthyl acetate | 1-Naphthylphosphate Disodium salt |
| Naphthol AS-acetate | 2-Naphthylphosphate Disodium salt |
| Naphthol AS-nonanoate | 2-Naphthylphosphate Sodium salt |
| 1-Naphthylbutyrate | 2-Naphthylphosphate Sodium salt |
| 2-Naphthylbutyrate | 1-Naphthylphosphate Sodium salt |
| 1-Naphthylcaprylate | Phenolphthalein diphosphate |
| 2-Naphthylcaprylate | Phenolphthalein diphosphate Tetrasodium salt |
| 2-Nitrophenyl-acetate | 5-Bromo-4-chloro-3-Indolyl-phosphate Disodium salt |
| 4-Nitrophenyl-acetate | 5-Bromo-4-chloro-3-Indolyl-phosphate Potassium salt |
| 2-Nitrophenyl-butyrate | 5-Bromo-4-chloro-3-Indolyl-phosphate p-Toluidine salt |
| 4-Nitrophenyl-butyrate | 3-Indoxyl-phosphate Di(2-amino-2-methyl-1,3-propanediol) salt |
| 4-Nitrophenyl-caprate | 3-Indoxyl-phosphate Disodium salt |
| 4-Nitrophenyl-caproate | 3-Indoxyl-phosphate p-Toluidine salt |
| 3-Nitrophenyl-caprylate | ALDOL 470 phosphate, disodium salt |
| 4-Nitrophenyl-caprylate | ALDOL 458 phosphate, disodium salt |
| 2-Nitrophenyl-myristate | |
| 4-Nitrophenyl-myristate | |
| 2-Nitrophenyl-palmitate | |
| 4-Nitrophenyl-palmitate | |
| 4-Nitrophenyl-propionate | |
| 4-Nitrophenyl-stearate | |
| 5-Bromo-4-chloro-3-Indolyl-acetate | |
| 5-Bromo-4-chloro-3-Indolyl-butyrate | |
| 5-Bromo-4-chloro-3-Indolyl-caprylate | |
| ALDOL 515 acetate | |
| ALDOL 470 acetate | |
| ALDOL 470 butyrate | |
| ALDOL 470 nanoate | |
| ALDOL 458 acetate | |

In a preferred embodiment, the culture device of the present disclosure comprises an indicator agent for detecting α-glucosidase enzyme activity, an indicator agent for detecting β-glucosidase enzyme activity, and an indicator agent for detecting β-galactosidase enzyme activity. In any embodiment, all three of the aforementioned indicator agents comprise similar or identical reporter groups. In a particularly preferred embodiment, the culture device of the present disclosure comprises 5-bromo-4-chloro-3-indolyl-α-D-glucopyranoside, 5-bromo-4-chloro-3-indolyl-β-D-glucopyranoside, and 5-bromo-4-chloro-3-indolyl-β-D-galactopyranoside.

According to the present disclosure, the indicator agents can be provided in the culture device as a powder or agglomerated powder (i.e., as a component of the cold-water-soluble first hydrogel-forming composition and/or the cold-water-soluble second hydrogel-forming composition described herein) or as a part of the first adhesive composition and/or second adhesive composition described herein. Advantageously, when provided in at least one of the adhesive compositions, the indicator agents can be uniformly distributed within the growth area of the culture device and can be provided in the adhesive composition at a very high concentration. Without being bound by theory, it is thought the indicator agents efficiently partition from the relatively hydrophobic adhesive composition into the relatively hydrophobic reconstituted gel, thereby providing consistent, uniform concentrations of the indicator agents to react with yeast or mold microorganisms, if present in the sample, in the culture device.

In any embodiment, the first and/or second adhesive composition can comprise five indicator agents. The five indicator agents can comprise 5-Bromo-4-chloro-3-indolyl acetate, 5-Bromo-4-chloro-3-indolyl-β-D-galactopyranoside, 5-Bromo-4-chloro-3-indolyl-β-D-glucopyranoside, 5-Bromo-4-chloro-3-indolyl-α-D-glucopyranoside, and 5-Bromo-4-chloro-3-indolyl phosphate p-toluidine salt. As shown in Table 13 below, the investigators have found this particular combination of indicator agents has the surprising effect of providing for the detection of at least one organism (e.g., a microorganism belonging to the genus Botrytis) that cannot otherwise be detected using a similar culture device having only one of the aforementioned indicator agents, indicating a possible synergistic effect of the combination.

In any embodiment, the first or second adhesive composition can comprise about 0.05-1.0 weight percent 5-Bromo-4-chloro-3-indolyl acetate, about 0.05-1.0 weight percent 5-Bromo-4-chloro-3-indolyl-β-D-galactopyranoside, 0.05-1.0 weight percent 5-Bromo-4-chloro-3-indolyl-β-D-glucopyranoside, about 0.05-1.0 weight percent 5-Bromo-4-chloro-3-indolyl-α-D-glucopyranoside and/or about 0.05-1.0 weight percent 5-Bromo-4-chloro-3-indolyl phosphate p-toluidine salt.

In any embodiment, the first or second adhesive composition can comprise about 0.18-0.5 weight percent 5-Bromo-4-chloro-3-indolyl acetate. In any embodiment, the first or second adhesive composition can comprise about 0.34-0.72 weight percent 5-Bromo-4-chloro-3-indolyl-β-D-galactopyranoside. In any embodiment, the first or second adhesive composition can comprise about 0.34-0.72 weight percent 5-Bromo-4-chloro-3-indolyl-β-D-glucopyranoside. In any embodiment, the first or second adhesive composition can comprise about 0.34-0.72 weight percent 5-Bromo-4-chloro-3-indolyl-α-D-glucopyranoside. In any embodiment, the first or second adhesive composition can comprise about 0.36-0.76 weight percent 5-Bromo-4-chloro-3-indolyl phosphate p-toluidine salt.

In any embodiment, the first or second adhesive composition can comprise about 0.18-0.5 weight percent 5-Bromo-4-chloro-3-indolyl acetate, about 0.34-0.72 weight percent 5-Bromo-4-chloro-3-indolyl-β-D-galactopyranoside, about 0.34-0.72 weight percent 5-Bromo-4-chloro-3-indolyl-β-D-glucopyranoside, about 0.34-0.72 weight percent 5-Bromo-4-chloro-3-indolyl-α-D-glucopyranoside, and about 0.36-0.76 weight percent 5-Bromo-4-chloro-3-indolyl phosphate p-toluidine salt.

Adhered to the first adhesive composition 20 is a cold-water-soluble first hydrogel-forming composition 22. The first hydrogel-forming composition 22 comprises at least one cold water soluble gelling agent. As indicated above, the dry medium can contain gelling agent only, and no nutrient. Optionally, in any embodiment, the first hydrogel-forming composition 22 also may comprise a nutrient for growing yeast or mold microorganisms. Suitable gelling agents for use in first hydrogel-forming composition 22 include cold-water-soluble natural and synthetic gelling agents. Non-limiting examples of suitable natural gelling agents include algin, carboxymethyl cellulose, hydroxyethyl cellulose, locust bean gum, xanthan gum. Suitable synthetic gelling agents include, for example polyacrylamide. Combinations of natural and/or synthetic gelling agents are contemplated. Preferred gelling agents include locust bean gum and xanthan gum, these gelling agents being useful individually or, in any embodiment, in combination with one another.

First hydrogel-forming composition 22 can contain the components discussed above in connection with dry media. Preferably, when gelling agent is included in first hydrogel-forming composition 22, it is included in an amount such that a predetermined quantity of water or an aqueous sample, e.g., 1 to 3 ml, placed on the medium will form a reconstituted medium having a suitable viscosity, e.g., about 1500 cps or more when measured at 60 rpm with a Brookfield Model L VF viscometer at 25° C. Media of this viscosity allow convenient handling and stacking of the devices during incubation and provide for distinct colony formation in the medium. For instance, 0.025 g to 0.050 g of powdered guar gum spread substantially uniformly over a surface area of 20.3 cm$^2$ will provide a sufficiently viscous medium when reconstituted with 1 to 3 ml of an aqueous sample. The size of the powder particles can be used to control the coating weight per unit area. For example, under conditions where a 100 mesh guar gum coats to a weight of about 0.05 g/20.3 cm$^2$, a 400 mesh guar gum coats to a weight of about 0.025 g/20.3 cm$^2$. The first hydrogel-forming composition can be applied to the first adhesive composition 20 using methods described in U.S. Pat. No. 5,089,413.

As indicated above, the dry medium can contain gelling agent only, and no nutrient. Before the addition of an aqueous sample liquid (e.g., a liquid sample suspected of containing yeast or mold microorganisms) to the culture device, the user can add nutrients tailored to the type of microorganisms to be grown. For example, dry powdered nutrients can be suspended in a rapidly-evaporating liquid such as ethanol or a volatile chlorofluorocarbon. In other instances, dry powdered nutrients can be suspended, e.g., dispersed or dissolved, in aqueous solutions. In either case, when an aliquot of the nutrient suspension or solution is added to the surface of the medium, the liquid can be allowed to evaporate, leaving ample nutrients along with the gelling agent. Additionally or alternatively, in any embodiment, one or more nutrient for growing yeast or mold microorganisms can be deposited into the culture device in an aqueous liquid (e.g., an aqueous suspending medium or diluent) when the culture device is inoculated.

The first and/or second hydrogel-forming composition (22 and 22', respectively) of the present disclosure further may comprise at least one nutrient to facilitate the growth of a yeast or mold microorganism. Yeast and mold microorganisms are metabolically and ecologically diverse and, thus, can utilize a variety of nutrients to support their growth and reproduction. Table 3 shows nonlimiting examples of genera that include yeast and mold microorganisms according to the present disclosure.

TABLE 3

Exemplary yeast and mold genera.

| Yeast genera | Mold genera |
| --- | --- |
| Candida | Alternaria |
| Cryptococcus | Aspergillus |
| Debaryomyces | Botrytis |
| Galactomyces | Cladosporium |
| Hanseniaspora | Colletotrichum |
| Issatchenkia | Fusarium |
| Kluyveromyces | Geotrichum |
| Metschnikowia | Monila |
| Pichia | Mucor |
| Rhodotorula | Penicillium |
| Saccharomyces | Pullularia |
| Saccharomycodes | Rhizopus |
| Schizosaccharomyces | Thamnidium |
| Sporobolomyces | Trichothecium |
| Torulaspora | |
| Trichosporon | |
| Zygosaccharomyces | |

Culture media (e.g., dehydrated, powdered culture media) comprising nutrients to facilitate the growth and reproduction of yeast and mold microorganisms are known in the art. Components of the culture media include, for example, a source of nitrogen (e.g., yeast extract, enzymatic digests of meat or other proteins, malt extract); a source of carbon (e.g., various sugars, polysaccharides, oligosaccharides, malt extract); one or more various inorganic salts (e.g., calcium chloride, ferric ammonium citrate, magnesium sulfate, manganese chloride, zinc sulfate); optionally, a buffering agent; and, optionally, an antibiotic such as tetracycline or chloramphenicol, for example, to inhibit the growth of bacteria. In view of the present disclosure, a person having ordinary skill in the art will recognize a variety of nutrient compositions that can be used with the enzyme substrate mixture of the present disclosure to detect yeast and mold microorganisms, provided a component of the nutrient composition does not substantially inhibit the hydrolysis of the enzyme substrates in the enzyme substrate mixture and provided a component of the nutrient composition does not substantially mask (e.g., by fluorescence quenching) the products of the enzyme substrates in the enzyme substrate mixture.

In any embodiment, the culture device can comprise a nutrient that includes proteins, oligopeptides, and/or amino acids. Non-limiting examples of such nutrients include yeast extract (e.g., yeast autolysate), malt extract, and peptic digest of meat.

In any embodiment, the culture device can comprise a carbohydrate nutrient comprising a monosaccharide, a disaccharide, a trisaccharide, an oligosaccharide, or a combination of any two or more of the foregoing. Those skilled in the art will also recognize that various sources of carbohydrates can be used. They can be natural sources (e.g., potato or plant extracts), as mixtures of natural sources, in pure forms (such as oligosaccharides or monosaccharides), in mixtures of pure forms, or as mixture of pure and natural forms. The natural mixtures can contain varying amounts of carbohydrates. Thus, carbohydrates may be provided from a variety of sources. Malt extract is an exemplary source of a variety of carbohydrates. In addition to comprising proteins, oligopeptides, and/or amino acids that facilitate the growth and reproduction of yeast and mold microorganisms, malt extract also comprises carbohydrate nutrients that facilitate the growth and reproduction of yeast and mold microorganisms.

The natural mixtures can contain various types and amounts of carbohydrates, such as polysaccharides, oligosaccharides, and monosaccharides. Polysaccharides that can be assimilated by yeasts and molds include soluble starch or inulin. Oligosaccharides that can be assimilated by yeasts and molds are sucrose, maltose, cellobiose, trehalose, lactose, melibiose, raffinose, and melezitose. Monosaccharides that can be metabolized by yeasts and molds include the hexoses (six carbon sugars): e.g., D-glucose, D-fructose, D-galactose, D-mannose, L-rhamnose, and L-sorbose; as well as the pentoses (five carbon sugars): e.g., D-xylose, D-ribose, L-arabinose, and D-arabinose.

Not all carbohydrates must be provided and the relative amount of each may vary. Those in the art will recognize that many different combinations of monosaccharides can be used in the culture medium of the present disclosure. Normally, only the sugars that can be metabolized by yeasts and molds are provided.

For general guidance, specific amounts of carbohydrates are indicated herein. These amounts are for general guidance only, and are determinable in accordance information known to those of skill in the art, and are not intended to be limiting. Those in the art will recognize that many different combinations of carbohydrates can be used in the culture device of the present disclosure. Normally, only those sugars which can be utilized by any particular yeasts and molds to be detected must be provided in the culture medium. Those skilled in the art will appreciate that other carbohydrates may be provided without departing from the invention.

In any embodiment, the culture device can comprise a buffering agent. The buffering agent can be provided in the first and/or second hydrogel-forming composition. Nonlimiting examples of suitable buffering agents include phosphate compounds (e.g., sodium dihydrogen phosphate, disodium hydrogen phosphate, potassium dihydrogen phosphate, dipotassium hydrogen phosphate), sodium carbonate, MOPS (2-[N-Morpholino]ethanesulfonic acid) free acid, and MOPS sodium salt.

The culture device of the present disclosure can comprise one or more inorganic element to facilitate the growth of yeast and/or molds. These include any one or more of the following (to the extent not already provided in the above sources of various components of the culture medium): calcium, chloride, cobalt, iron, manganese, phosphorus, potassium, sulfur, sodium, tin, and zinc. Salts may be provided as a source of ions. Salts may include (amounts per liter of medium): potassium phosphate, magnesium sulfate, sodium chloride, calcium chloride, boric acid, copper sulfate, potassium iodide, ferric chloride, manganese sulfate, sodium molybdate, and zinc sulfate. The inorganic element(s) and/or salt(s) can be provided in the first powder and/or second powder, if present.

In any embodiment, a culture device of the present disclosure may further comprise a selective agent. In order to grow a yeast or mold sample without interference from bacteria, bacteriostatic or bactericidal selective agents such as chloramphenicol, chlortetracycline, tartaric acid, or suitable penicillin, for example, can be included. The selective agent may be provided in the first hydrogel-forming composition and/or second hydrogel-forming composition, if present. Alternatively or additionally, a selective agent may be provided in the first adhesive composition and/or second adhesive composition, if present.

In another aspect, the present disclosure provides a method of detecting a yeast or mold microorganism. The method comprises contacting a sample and an aqueous liquid with the gelling agent disposed on the first or second adhesive composition of any embodiment of the culture device disclosed herein. In any embodiment, the sample can comprise the aqueous liquid. In general, the amounts of gelling agent; indicator agents; and nutrient (if present) in the culture device are selected to provide an effective concentration for detecting yeast or mold microorganisms when they are reconstituted with a predetermined volume (e.g., 1 milliliter, 2 milliliters, 5 milliliters) of aqueous liquid. The aqueous liquid can be added with the sample materials (e.g., the sample material can be dissolved, homogenized, suspended, and/or diluted in an aqueous liquid such as sterile water, an aqueous buffer, or an aqueous nutrient medium, for example). In any embodiment wherein the sample comprises solid (e.g., a membrane filter having retained material thereon or therein) or semisolid materials, the predetermined volume of liquid (e.g., sterile water, an aqueous nutrient medium) can be used to reconstitute the culture device before or after the solid or semisolid sample is used to inoculate the device.

The sample can be contacted with the gelling agent using methods that are known in the art (e.g., by pouring or pipetting a liquid sample onto the gelling agent). In an embodiment where the culture device comprises a coversheet, the coversheet is typically lifted to permit deposition of the sample between the coversheet and the substrate; preferably, into the aperture of a spacer, if present, in the culture device. In any embodiment, contacting a sample and an aqueous liquid with the gelling agent forms an inoculated culture device. After forming the inoculated culture device, the coversheet, if present, is lowered to form a protective barrier against contamination and/or excess evaporation of the aqueous liquid during incubation. In any embodiment, the sample may be spread evenly over the growth region, for example by placing a weighted plate on top of the covered device. If the coversheet is not present, preferably, the inoculated culture device is placed in a sterile container to prevent contamination and/or excessive evaporation of the aqueous liquid during incubation.

The embodiment of device 11 illustrated in FIG. 3 is identical to that of FIG. 2 except that spacer 24 is not present in FIG. 3. To use such an embodiment, a template (e.g., a weighted circular ring defining the growth region) can be applied temporarily on top of coversheet 18, after closing, to confine reconstitution of the medium to the growth region of the medium.

In any embodiment, contacting a sample with the gelling agent disposed on the first or second adhesive composition of the culture device comprises placing the sample in fluid communication with the at least one nutrient. This can be achieved by suspending or diluting the sample in a liquid (e.g., an aqueous liquid) comprising a nutrient or by contacting the sample and an aqueous liquid with a first hydrogel-forming composition or second hydrogel-forming composition, described herein, comprising the at least one nutrient.

In any embodiment, the method further comprises incubating (e.g., in a temperature-controlled environmental chamber) the inoculated culture device for a period of time. The incubation conditions (e.g., the incubation temperature) can affect the rate of growth of yeast and mold microorganisms present in the sample. A person having ordinary skill in the art will recognize suitable incubation temperatures to detect specific yeast and mold microorganisms. An inoculated culture device of the present disclosure can be incubated, for example at temperatures between about 20° C. to about 32° C., inclusive. In any embodiment, the culture device can be incubated under aerobic conditions.

The inoculated culture device is incubated for a period of time sufficient to permit the growth of a yeast or mold microorganism. In any embodiment, the period of time can be about 36 hours to about 120 hours, inclusive. In any embodiment, the period of time can be about 48 hours to about 120 hours, inclusive. In any embodiment, the period of time can be about 48 hours to about 96 hours, inclusive. In any embodiment, the period of time can be about 48 hours to about 72 hours, inclusive. In any embodiment, the period of time can be about 48 hours to about 48 hours, inclusive. In any embodiment, the period of time can be up to about 72 hours. In any embodiment, the period of time can be up to about 60 hours. In any embodiment, the period of time can be up to about 48 hours.

The method of the present disclosure further comprises detecting a yeast or mold colony in the culture device (e.g., observing a yeast or mold colony in the culture device). In any embodiment, detecting a yeast or mold colony in the culture device can comprise detecting in the culture device a presence or an absence of the detectable reporter group of at least one of the indicator agents, wherein detecting the presence of the detectable reporter group is indicative of a presence of a colony of yeast or mold microorganisms. As a yeast or mold colony grows in the culture device of the present disclosure, the cells in the colony react with one or more of the indicator agents to activate (e.g., by hydrolysis of a chromogenic or fluorogenic enzyme substrate) the reporter group thereby directly or indirectly making the reporter group detectable. In the case of chromogenic indicator agents, the reporter group can be detected by the characteristic wavelengths of light that it absorbs and/or reflects. For example, indicator agents comprising an indolyl reporter group can dimerize to form indigo or derivatives thereof. Thus, the presence of a colony having a color (e.g., either the colony having the color or the hydrogel proximate the colony having the color) that is associated with a particular reporter group is indicative of a colony of yeast or mold microorganisms.

In the case of fluorogenic indicator agents, the detectable reporter group can be observed by illuminating the culture device with an appropriate wavelength of light (e.g., about 365 nm to detect a reporter group comprising 4-methylumbelliferone) and observing the light emitted by the reporter group. A person having ordinary skill in the art will recognize suitable wavelengths of light required respectively to illuminate the culture device and to detect a reporter group associated with a particular fluorogenic indicator agent. A colony having the color of the fluorescent reporter group or the presence of the fluorescent reporter group in the hydrogel proximate the colony is in indication the colony is a yeast colony or a mold colony.

In any embodiment, detecting the reporter group can comprise observing the culture device visually. In any embodiment, detecting the reporter group can comprise obtaining an image of the culture device and observing the image visually or analyzing the image using automated image-analysis techniques. Methods and devices for automated detection of microbial colonies in a culture device are described, for example, in U.S. Pat. Nos. 5,448,652; 6,058,209; 6,243,486; 6,271,022; 7,298,885; and 7,319,031; which are all incorporated herein by reference in their entirety.

In any embodiment, the method of the present disclosure further comprises enumerating yeast or mold colonies present in the inoculated culture device after incubating the inoculated culture device. Thus, after the yeast or mold colonies are detected as described herein, the number of detected colonies is determined either manually or using automated processes known in the art.

EMBODIMENTS

Embodiment A is a culture device, comprising:
a body comprising a self-supporting substrate having a first major surface and a second major surface;
a first adhesive composition disposed on a portion of the first major surface of the substrate;
a substantially dry, cold-water-soluble first hydrogel-forming composition adhered to the first adhesive composition; and
a plurality of indicator agents, the plurality of indicator agents comprising:
  three indicator agents for detecting distinct glycosidase enzyme activities;
  an indicator agent for detecting an alkyl esterase enzyme activity;
  an indicator agent for detecting a phosphatase enzyme activity;
wherein each of the plurality of indicator agents comprises a detectable reporter group.

Embodiment B is the culture device of Embodiment A, further comprising a cover sheet attached to the body member.

Embodiment C is the culture device of Embodiment B, wherein the cover sheet comprises a first major surface facing the body member; wherein the culture device further comprises a second adhesive composition disposed on a portion of the first major surface of the cover sheet and a substantially dry, cold-water-soluble second hydrogel-forming composition adhered to the second adhesive composition.

Embodiment D is the culture device of any one of the preceding Embodiments, wherein at least one of the plurality of indicator agents is disposed in the first adhesive composition, the second adhesive composition, the first hydrogel-forming composition, and/or the second hydrogel-forming composition.

Embodiment E is the culture device of Embodiment D, wherein at least three of the plurality of indicator agents are disposed in the first adhesive composition and/or the second adhesive composition.

Embodiment F is the culture device of Embodiment E, wherein at least five of the indicator agents are disposed in the first adhesive composition and/or the second adhesive composition.

Embodiment G is the culture device of any one of the preceding Embodiments, further comprising an air-permeable membrane disposed between the substrate and the first hydrogel-forming composition.

Embodiment H is the culture device of any one of the preceding Embodiments, wherein the at least three indicator agents for detecting distinct glycosidase enzyme activities include a compound to detect alpha-glucosidase enzyme activity, a compound to detect beta-glucosidase enzyme activity, and a compound to detect beta-galactosidase enzyme activity.

Embodiment I is the culture device of any one of the preceding Embodiments, wherein at least one of the plurality of indicator agents is a chromogenic enzyme substrate or fluorogenic enzyme substrate.

Embodiment J is the culture device of Embodiment I, wherein each of the plurality of indicator agents is a chromogenic enzyme substrate or fluorogenic enzyme substrate.

Embodiment K is the culture device of any one of the preceding Embodiments, wherein the at least three indicator agents for detecting distinct glycosidase enzyme activities comprise 5-bromo-4-chloro-3-indolyl-beta-D-galactopyranoside, 5-bromo-4-chloro-3-indolyl-alpha-D-glucopyranoside, and 5-bromo-4-chloro-3-indolyl-beta-D-glucopyranoside.

Embodiment L is the culture device of any one of the preceding Embodiments, wherein the indicator agent for detecting an alkyl esterase enzyme activity comprises 3-indolyl-acetate.

Embodiment M is the culture device of Embodiment L, wherein the indicator agent for detecting an alkyl esterase enzyme activity comprises 5-bromo-4-chloro-3-indolyl-acetate.

Embodiment N is the culture device of any one of the preceding Embodiments, wherein the indicator agent for detecting a phosphatase enzyme activity comprises 5-bromo-4-chloro-3-indolyl-phosphate.

Embodiment O is the culture device of any one of the preceding Embodiments, further comprising a water-insoluble spacer having an aperture, the spacer being attached to the body member or the coversheet and the entire aperture being positioned between the body member and the cover sheet.

Embodiment P is the culture device of any one of the preceding Embodiments, further comprising a predefined volume of aqueous liquid disposed between the body member and the coversheet, wherein the aqueous liquid and gelling agent form a hydrogel.

Embodiment Q is the culture device of Embodiment P, wherein the at least one nutrient comprises malt extract.

Embodiment R is the culture device of Embodiment P or Embodiment Q, wherein the at least one nutrient is selected from the group consisting of a peptic digest of meat, yeast extract, dextrose, potassium phosphate, ferric ammonium citrate, magnesium sulfate, manganese chloride, sodium carbonate, zinc sulfate, or a combination of any two or more of the foregoing nutrients.

Embodiment S is the culture device of any one of the preceding Embodiments, wherein the first hydrogel-forming composition or the second hydrogel-forming composition comprises substantially dry agglomerated powders.

Embodiment T is the culture device of Embodiment S, wherein at least one of the plurality of indicator agents is disposed in the second adhesive composition.

Embodiment U is the culture device of Embodiment O as dependent on Embodiment N, wherein the spacer comprises a perimeter that defines a growth area and a thickness dimension, wherein the thickness dimension is selected to prevent contact between hydrogel and the coversheet in the growth area.

Embodiment V is the culture device of any one of the preceding Embodiments, further comprising a selective agent disposed in the first adhesive composition or the second adhesive composition.

Embodiment W is a method of detecting yeast and mold in a sample, comprising:
contacting a sample and an aqueous liquid with the gelling agent disposed on the first or second adhesive composition of the culture device of any one of Embodiments A through V to form an inoculated culture device;
incubating the inoculated culture device for a period of time; and
detecting a yeast or mold colony in the culture device.

Embodiment X is the method of Embodiment W, wherein detecting a yeast or mold colony in the culture device comprises detecting in the culture device a presence or an absence of the detectable reporter group of at least one of the indicator agents, wherein detecting the presence of the detectable reporter group is indicative of a presence of a colony of yeast or mold microorganisms.

Embodiment Y is the method of Embodiment W or Embodiment X, wherein contacting a sample with the gelling agent disposed on the first or second adhesive composition of the culture device comprises placing the sample in fluid communication with the at least one nutrient.

Embodiment Z is the method of any one of Embodiments W through Y, wherein incubating the inoculated culture device comprises incubating the inoculated culture device at a temperature between about 20° C. and about 32° C., inclusive.

Embodiment AA is the method of any one of Embodiments W through Z, wherein incubating the inoculated culture device for a period of time comprises incubating the inoculated culture device for up to about 72 hours.

Embodiment BB is the method of Embodiment AA, wherein incubating the inoculated culture device for a period of time comprises incubating the inoculated culture device for up to about 60 hours.

Embodiment CC is the method of Embodiment BB, wherein incubating the inoculated culture device for a period of time comprises incubating the inoculated culture device for up to about 48 hours.

Embodiment DD is the method of any one of Embodiments W through CC, further comprising enumerating yeast or mold colonies present in the inoculated culture device after incubating the inoculated culture device.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Indicators

The chromogenic substrate indicators that were used in the examples are listed in Table 4 and were purchased from Biosynth International, Inc. (Itasca, Ill.).

TABLE 4

| Indicator Name | CAS Number |
| --- | --- |
| 5-Bromo-4-chloro-3-indolyl acetate (X-3-Acetate) | 3252-36-6 |
| 5-Bromo-4-chloro-3-indolyl-beta-D-galactopyranoside (X-Gal) | 7240-90-6 |
| 5-Bromo-4-chloro-3-indolyl-beta-D-glucopyranoside (X-b-Glu) | 15548-60-4 |
| 5-Bromo-4-chloro-3-indolyl-alpha-D-glucopyranoside (X-a-Glu) | 108789-36-2 |
| 5-Bromo-4-chloro-3-indolyl phosphate para-toluidine salt (BCIP p-toluidine) | 6578-06-9 |

Each of the Indicator Coating Formulations A-D (Table 5) was prepared from the five chromogenic substrate indicators in the amounts specified in Table 5 and 100 g of a noninhibitory adhesive copolymer of isooctyl acrylate and acrylamide (described below).

TABLE 5

| | Indicator Coating Formulations A-D: Chromogenic Substrate Indicator Composition (mg) of the Indicator Coating Formulation | | | |
| --- | --- | --- | --- | --- |
| | A | B | C | D |
| X-3-Acetate | 43.3 | 57.7 | 57.7 | 121.2 |
| X-Gal | 81.8 | 81.8 | 81.8 | 171.8 |
| X-b-Glu | 81.8 | 81.8 | 81.8 | 171.8 |
| X-a-Glu | 81.8 | 81.8 | 81.8 | 171.8 |
| BCIP p-toluidine | 173.3 | 130.0 | 86.7 | 182.0 |

Culture Media Formulations

Six separate culture media formulations were prepared as homogeneous mixtures by blending the formulation ingredients together. The compositions of Culture Media Formulations E-J are described in Tables 6-11.

TABLE 6

Culture Media Formulation E

| Ingredient | Amount (grams) | Source |
| --- | --- | --- |
| Peptic digest of animal tissue | 6.3 g | Alpha Biosciences (Baltimore, MD) |
| Magnesium sulfate | 0.6 g | EMD Millipore (Billerica, MA) |
| Ferric ammonium citrate | 0.3 g | Sigma-Aldrich (St. Louis, MO) |
| Calcium chloride | 0.1 g | Mallinckrodt (St. Louis, MO) |
| Potassium phosphate monobasic | 1.3 g | EMD Millipore (Billerica, MA) |
| Sodium carbonate | 0.2 g | Sigma-Aldrich (St. Louis, MO) |
| Dextrose | 11.3 g | Becton, Dickinson (New Franklin, NJ) |
| Total Ingredients | 20.1 g | |

TABLE 7

Culture Media Formulation F

| Ingredient | Amount (grams) | Source |
| --- | --- | --- |
| Peptic digest of animal tissue | 7.1 g | Alpha Biosciences (Baltimore, MD) |
| Yeast extract | 4.3 g | Alpha Biosciences (Baltimore, MD) |
| Magnesium sulfate | 0.7 g | EMD Millipore (Billerica, MA) |
| Ferric ammonium citrate | 0.4 g | Sigma-Aldrich (St. Louis, MO) |
| Calcium chloride | 0.1 g | Mallinckrodt (St. Louis, MO) |
| Sodium carbonate | 0.2 g | Sigma-Aldrich (St. Louis, MO) |
| Dextrose | 7.1 g | Becton, Dickinson (New Franklin, NJ) |
| Total Ingredients | 19.9 g | |

TABLE 8

Culture Media Formulation G

| Ingredient | Amount (grams) | Source |
| --- | --- | --- |
| Peptic digest of animal tissue | 6.6 g | Alpha Biosciences (Baltimore, MD) |
| Malt extract | 4.9 g | EMD Millipore (Billerica, MA) |
| Yeast extract | 1.6 g | Alpha Biosciences (Baltimore, MD) |
| Magnesium sulfate | 1.0 g | EMD Millipore (Billerica, MA) |
| Ferric ammonium citrate | 0.6 g | Sigma-Aldrich (St. Louis, MO) |
| Calcium chloride | 0.1 g | Mallinckrodt (St. Louis, MO) |
| Zinc sulfate | 0.7 g | EMD Millipore (Billerica, MA) |
| Potassium phosphate monobasic | 0.5 g | EMD Millipore (Billerica, MA) |
| Sodium carbonate | 0.2 g | Sigma-Aldrich (St. Louis, MO) |
| Dextrose | 3.9 g | Becton, Dickinson (New Franklin, NJ) |
| Total Ingredients | 20.1 g | |

TABLE 9

Culture Media Formulation H

| Ingredient | Amount (grams) | Source |
| --- | --- | --- |
| Peptic digest of animal tissue | 7.0 g | Alpha Biosciences (Baltimore, MD) |
| Malt extract | 4.5 g | EMD Millipore (Billerica, MA) |
| Calcium chloride | 0.1 g | Mallinckrodt (St. Louis, MO) |
| Manganese chloride | 0.1 g | Alfa Aesar (Ward Hill, MA) |
| Yeast extract | 2.5 g | Alpha Biosciences (Baltimore, MD) |

TABLE 9-continued

Culture Media Formulation H

| Ingredient | Amount (grams) | Source |
|---|---|---|
| Magnesium sulfate | 0.1 g | EMD Millipore (Billerica, MA) |
| Ferric ammonium citrate | 0.2 g | Sigma-Aldrich (St. Louis, MO) |
| Zinc sulfate | 0.1 g | EMD Millipore (Billerica, MA) |
| Potassium phosphate monobasic | 0.5 g | EMD Millipore (Billerica, MA) |
| Sodium carbonate | 0.1 g | Sigma-Aldrich (St. Louis, MO) |
| Dextrose | 5.0 g | Becton, Dickinson (New Franklin, NJ) |
| Total Ingredients | 20.2 g | |

TABLE 10

Culture Media Formulation I

| Ingredient | Amount (grams) | Source |
|---|---|---|
| Proteose peptone | 5.0 g | Becton, Dickinson (New Franklin, NJ) |
| Casein | 3.1 g | Becton, Dickinson (New Franklin, NJ) |
| Peptic casein digest | 1.2 g | Becton, Dickinson (New Franklin, NJ) |
| Yeast extract | 1.9 g | Alpha Biosciences (Baltimore, MD) |
| Ferric ammonium citrate | 0.2 g | Sigma-Aldrich (St. Louis, MO) |
| Calcium chloride | 0.1 g | Mallinckrodt (St. Louis, MO) |
| Sodium carbonate | 0.1 g | Sigma-Aldrich (St. Louis, MO) |
| Dextrose | 8.5 g | Becton, Dickinson (New Franklin, NJ) |
| Total Ingredients | 20.1 g | |

TABLE 11

Culture Media Formulation J

| Ingredient | Amount (grams) | Source |
|---|---|---|
| Malt extract | 20.0 g | EMD Millipore (Billerica, MA) |
| Total Ingredients | 20.0 g | |

Inoculation and Incubation

With the exception of *S. cerevisiae*, *H. anomala*, and *C. albicans*, the yeast and mold strains that were used in the examples (and listed in Table 12) were purchased as lyophilized discs from MicroBiologics, Inc. (St. Cloud, Minn.). The strains of *S. cerevisiae*, *H. anomala*, and *C. albicans* were purchased as KWIK STIK devices from MicroBiologics, Inc., and were propagated according to the manufacturer's instructions. A single lyophilized disc of each strain was separately added to 10 to 30 milliliters of 0.1% peptone water (Catalog No. D299, Hardy Diagnostics, Santa Maria, Calif.) to resuspend the organisms from the lyophilized disc material. The samples were each serially diluted in 0.1% peptone water to yield concentrations that provided counts of colony forming units (cfu) within the counting range of the thin film culture device (approximately 15-150 cfu per device).

Dichloran Rose Bengal Chloramphenicol (DRBC) Agar Petri dish plates were prepared as reference culturing devices (Becton Dickinson Company, Franklin Lakes, N.J.). A 100 microliter aliquot of inoculum was spread plated onto the DRBC plate and the plate was incubated at 25° C. for 5 days. The counts obtained with the DRBC reference plate were multiplied by a dilution factor of 10 to account for the differences in inoculum volume added to the DRBC reference plates and the experimental thin film culture plates.

TABLE 12

Yeast and Mold Strains

*Paecilomyces* spp. (3M-M10)
*Saccharomyces cerevisiae* (ATCC 7754)
*Botrytis* spp. (3M-M97)
*Hansenula anomala* (3M-Y28)
*Candida albicans* (ATCC 10231)
*Penicillium chrysogenum* (ATCC 10106)
*Trichosporon mucoides* (ATCC 201382)
*Candida guilliermondii* (ATCC 6260)
*Aspergillus niger* (3M-M6)

Example 1

The Indicator Coating Formulation B (Table 5) was prepared by mixing the five chromogenic substrate indicators in DMSO (5-15 mL) and then adding to 100 g of the noninhibitory adhesive copolymer (approximately 24% solids in a solution in ethyl acetate and heptanes) described in Example 1 of U.S. Pat. No. 5,635,367, which is incorporated herein by reference in its entirety. The resulting coating formulation was stirred until homogeneous. The formulation was knife coated (gap setting of about 1 mil) onto one side of a 1.6 mil thick bi-axially oriented polypropylene (BOPP) film substrate (Vifan Company, Morristown, Tenn.). The coated film was dried in an oven at 70-80° C. for 10-15 minutes. The coated side of the BOPP film was then powder coated with a 1:1 mixture of xanthan gum and locust bean gum. The excess powder was shaken loose.

The thin film culture device for the experiment was prepared by removing the thin film cover sheet from a commercially available 3M PETRIFILM Yeast & Mold Count Pate (3M Company) and replacing it with the coated BOPP film described above. The coated BOPP film was cut to the same dimensions as the bottom film and was it was oriented so that the coated surface of the film faced the culture medium. The new thin film cover sheet containing the five indicators was attached to the bottom film using double-sided tape.

The thin film culture devices were inoculated with a single yeast or mold sample selected from *Paecilomyces* spp., *Saccharomyces cerevisiae*, *Botrytis* spp., *Hansenula anomala*, *Candida albicans*, *Penicillium chrysogenum*. The top film of the device was lifted up and 1 mL of the inoculum was added (by pipet) to the culture medium on the bottom film. The top film was replaced and the sample was uniformly distributed to the desired area (30 mm$^2$) using a 3M PETRIFILM Flat Spreader (3M Company). Duplicate thin film culture devices were prepared for each sample. The inoculated devices were incubated at 25° C. for 60 to 72 hours.

The colonies in each device were counted by visual examination at 48 hours and at the end of the incubation period (60-72 hour timepoint). At each timepoint, the cfu counts of the individual devices were averaged and the average count value was determined. The colonies on reference DRBC plates were counted in the same manner as described for the thin film culture devices. The results for the 48 hour time point are presented in Tables 13 and 14 together with the results obtained for Comparative Examples 1-6 and for the DRBC reference plates. The cfu counts for the DRBC plates were taken after 5 days of incubation.

Comparative Example 1

The same procedure as described in Example 1 was used with the exception that only a single indicator agent, 5-bromo-4-chloro-3-indolyl acetate (57.7 mg per 100 g of adhesive), was included in the top film coating (instead of five indicator agents). For each yeast or mold sample, the device was inoculated with the same sample preparation as used in Example 1. The results are presented in Tables 13 and 14.

Comparative Example 2

The same procedure as described in Example 1 was used with the exception that only a single indicator agent, 5-bromo-4-chloro-3-indolyl-beta-D-galactopyranoside (81.8 mg per 100 g of adhesive), was included in the top film coating (instead of five indicator agents). For each yeast or mold sample, the device was inoculated with the same sample preparation as used in Example 1. The results are presented in Tables 13 and 14.

Comparative Example 3

The same procedure as described in Example 1 was used with the exception that only a single indicator agent, 5-bromo-4-chloro-3-indolyl-beta-D-glucopyranoside (81.8 mg per 100 g of adhesive), was included in the top film coating (instead of five indicator agents). For each yeast or mold sample, the device was inoculated with the same sample preparation as used in Example 1. The results are presented in Tables 13 and 14.

Comparative Example 4

The same procedure as described in Example 1 was used with the exception that only a single indicator agent, 5-bromo-4-chloro-3-indolyl-alpha-D-glucopyranoside (81.8 mg per 100 g of adhesive), was included in the top film coating (instead of five indicator agents). For each yeast or mold sample, the device was inoculated with the same sample preparation as used in Example 1. The results are presented in Tables 13 and 14.

Comparative Example 5

The same procedure as described in Example 1 was used with the exception that only a single indicator agent, 5-bromo-4-chloro-3-indolyl phosphate para-toluidine salt (130 mg per 100 g of adhesive), was included in the top film coating (instead of five indicator agents). For each yeast or mold sample, the device was inoculated with the same sample preparation as used in Example 1. The results are presented in Tables 13 and 14.

TABLE 13

| | Average Colony Count (cfu) | | |
|---|---|---|---|
| | *Paecilomyces* spp. | *Penicillium chrysogenum* | *Botrytis* spp. |
| Example 1 | 73 | 247 | 60 |
| Comparative Example 1 | 35 | 250 | 0 |
| Comparative Example 2 | 50 | 0 | 0 |
| Comparative Example 3 | 0 | 0 | 0 |
| Comparative Example 4 | 0 | 0 | 0 |
| Comparative Example 5 | 0 | 0 | 0 |
| Reference Example (DRBC agar) | 50 | 220 | 50 |

TABLE 14

| | Average Colony Count (cfu) | | |
|---|---|---|---|
| | *Hansenula anomala* | *Candida albicans* | *Saccharomyces cerevisiae* |
| Example 1 | 491 | 430 | 90 |
| Comparative Example 1 | 301 | 251 | 60 |
| Comparative Example 2 | 0 | 0 | 0 |
| Comparative Example 3 | 427 | 0 | 0 |
| Comparative Example 4 | 416 | 410 | 60 |
| Comparative Example 5 | 384 | 0 | 0 |
| Reference Example (DRBC agar) | 280 | 460 | 35 |

Example 2

The thin film culture devices were prepared using the general procedures described in U.S. Pat. Nos. 4,565,783 and 5,089,413. The coating formulation was prepared by adding a solution containing 5-bromo-4-chloro-3-indolyl phosphate para-toluidine salt (86.7 mg), chlortetracycline (13.6 mg), and chloramphenicol (10.9 mg) in methanol (5-10 mL) to 100 g of the acrylate copolymer adhesive described in Example 1. The resulting coating formulation was stirred until homogeneous. The coating substrate was a microporous polyolefin film (Tredegar EXXAIRE film, Tredegar Film Products, Richmond, Va.) adhesively laminated to polysilk paper. The coating formulation was knife coated (gap setting of about 1 mil) onto the microporous polyolefin film side of the substrate to create a master roll. The master roll was cut into 76 mm wide by 102 mm long sections that formed the bottom layer of the device. A foam layer (76 mm wide by 102 mm long by 0.57 mm thick) with a circular opening (61 mm in diameter) was adhesively laminated to the coated side of the bottom film. The circular opening was positioned in the center of the foam layer.

The culture medium was prepared by adding a mixture of xanthan gum and locust bean gum (1:1 by weight) to the pre-blended Culture Media Formulation E (described in Table 6) in a ratio of three parts gum mixture to one part Culture Media Formulation E. The combined mixture was blended to complete the mixing. Approximately two grams of the combined powder mixture was evenly applied to cover the adhesive exposed by the circular opening in the thin film culture device. Excess powder was removed by inverting the device. The result was a thin layer of the combined powder mixture (culture medium and gum) bonded to the adhesive layer of the device.

The thin film cover sheet containing Indicator Coating Formulation B was prepared according to the procedure described in Example 1. The coated cover sheet was cut to the same dimensions as the bottom film section and was it was oriented so that the coated surface of the cover sheet faced the culture medium. The cover sheet was attached to the bottom film using double-sided tape.

The thin film culture devices were inoculated with a single yeast sample selected from *Candida albicans, Trichosporon mucoides, Candida guilliermondii*. The top film of the device was lifted up and 1 mL of the inoculum was added (by pipet) to the culture medium on the bottom film. The top film was replaced and the sample was uniformly spread to the edges of the circular opening by applying downward pressure with a 3M PETRIFILM Flat Spreader. Duplicate thin film culture devices were prepared for each sample. The inoculated devices were incubated at 25° C. for 60 to 72 hours.

The colonies from each sample were counted by visual examination at 48 hours and at the end of the incubation period (60-72 hour timepoint). The colonies were either white or blue in color. At each timepoint, the cfu counts of the individual devices were averaged and the average count value was used to calculate the number of colony forming units per milliliter (cfu/mL) in the original undiluted sample. The calculated cfu/mL values and colony color (white or blue) for each sample at the 48 hour timepoint are reported in Table 15 together with the results obtained for Examples 3-6.

Example 3

The same experimental conditions and procedures as described in Example 2 were followed with the exception that the thin film culture devices were prepared using Culture Media Formulation F (described in Table 7), instead of Culture Media Formulation E (described in Table 6).

Example 4

The same experimental conditions and procedures as described in Example 2 were followed with the exception that the thin film culture devices were prepared using Culture Media Formulation G (described in Table 8), instead of Culture Media Formulation E (described in Table 6).

Example 5

The same experimental conditions and procedures as described in Example 2 were followed with the exception that the thin film culture devices were prepared using Culture Media Formulation H (described in Table 9), instead of Culture Media Formulation E (described in Table 6).

Example 6

The same experimental conditions and procedures as described in Example 2 were followed with the exception that the thin film culture devices were prepared using Culture Media Formulation I (described in Table 10), instead of Culture Media Formulation E (described in Table 6).

Example 7

The same experimental conditions and procedures as described in Example 2 were followed with the exception that the thin film culture devices were prepared using Culture Media Formulation J (described in Table 11), instead of Culture Media Formulation E (described in Table 6).

TABLE 15

| | Culture Media Formulation | cfu/mL (colony color) | | |
|---|---|---|---|---|
| | | *Candida albicans* | *Trichosporon mucoides* | *Candida guilliermondii* |
| Example 2 | E | $2.1 \times 10^7$ (blue) | $9.6 \times 10^5$ (blue) | $1.6 \times 10^7$ (white) |
| Example 3 | F | $2.0 \times 10^7$ (blue) | $1.1 \times 10^6$ (blue) | $1.8 \times 10^7$ (white) |
| Example 4 | G | $2.2 \times 10^7$ (blue) | $7.2 \times 10^5$ (blue) | $1.6 \times 10^7$ (blue) |
| Example 5 | H | $2.0 \times 10^7$ (blue) | $7.6 \times 10^5$ (blue) | $1.0 \times 10^7$ (blue) |
| Example 6 | I | $3.3 \times 10^7$ (white) | $7.2 \times 10^5$ (white) | $1.7 \times 10^7$ (white) |
| Example 7 | J | NT | $8.5 \times 10^5$ (blue) | $2.0 \times 10^7$ (light blue) |

Example 8

The thin film culture devices as described in Example 2 were prepared with two exceptions. First, the thin film culture devices were prepared using Culture Media Formulation H (described in Table 9), instead of Culture Media Formulation E (described in Table 6). Second, the thin film cover sheet of the device was coated with Indicator Coating Formulation A, instead of Indicator Coating Formulation B.

The thin film culture devices were inoculated with a single yeast or mold sample selected from *Paecilomyces* spp., *Saccharomyces cerevisiae, Botrytis* spp., *Hansenula anomala, Candida albicans, Penicillium chrysogenum, Aspergillus niger*. The top film of the device was lifted up and 1 mL of the inoculum was added (by pipet) to the culture medium on the bottom film. The top film was replaced and the sample was uniformly spread to the edges of the circular opening by applying downward pressure with a 3M PETRIFILM Flat Spreader. Duplicate thin film culture devices were prepared for each sample. The inoculated devices were incubated at 25° C. for 48 to 60 hours.

The colonies from each sample were counted by visual examination at either the 48 hour or 60 hour timepoint. The cfu counts of the individual devices were averaged and the average count value was used to calculate the number of colony forming units per milliliter (cfu/mL) in the original undiluted sample. In Tables 16 and 17, the calculated cfu/mL values for each sample at either the 48 hour or 60 hour timepoint are presented.

Example 9

The same experimental conditions and procedures as described in Example 8 were followed with the exception that the thin film cover sheet of the device was coated with Indicator Coating Formulation B, instead of Indicator Coating Formulation A. The results are presented in Tables 16 and 17.

Example 10

The same experimental conditions and procedures as described in Example 8 were followed with the exception that the thin film cover sheet of the device was coated with Indicator Coating Formulation C, instead of Indicator Coating Formulation A. The results are presented in Tables 16 and 17.

TABLE 16

Colony counts after 48 hours of incubation

| Indicator Coating Formulation | Hansenula anomala | cfu/mL Saccharomyces cerevisiae | Candida albicans |
|---|---|---|---|
| Example 8 | A | $6.5 \times 10^7$ | $1.1 \times 10^7$ | $3.9 \times 10^7$ |
| Example 9 | B | $4.7 \times 10^6$ | $2.5 \times 10^6$ | $1.1 \times 10^8$ |
| Example 10 | C | $1.5 \times 10^6$ | $9.4 \times 10^5$ | $2.4 \times 10^5$ |

TABLE 17

Colony counts after 48 or 60 hours of incubation (as designated).

| Indicator Coating Formulation | Paecilomyces spp. | Botrytis spp. | Aspergillus niger | Penicillium chrysogenum |
|---|---|---|---|---|
| Example 8 | A | $6.5 \times 10^4$ (a) | $4.6 \times 10^4$ (b) | $2.0 \times 10^4$ (b) | $4.5 \times 10^6$ (a) |
| Example 9 | B | $8.4 \times 10^4$ (a) | $5.2 \times 10^4$ (a) | $2.8 \times 10^4$ (a) | $3.1 \times 10^6$ (b) |
| Example 10 | C | $6.6 \times 10^4$ (a) | $6.0 \times 10^4$ (a) | $3.3 \times 10^4$ (a) | $3.4 \times 10^6$ (a) |

(a) Colony counted after 48 hours of incubation.
(b) Colony counted after 60 hours of incubation.

Example 11

The same thin film culture devices as described in Example 8 were prepared with the exception that the thin film cover sheet of the device was coated with Indicator Coating Formulation D, instead of Indicator Coating Formulation A.

Six food items were selected for testing (corn kernels, cut carrots, tomato paste, green chili puree, pasta in meat sauce, and chicken seasoning). Each food item was tested separately. An 11 g portion of the food sample was added to a plastic enrichment bag containing 99 mL of 0.1% peptone water and the bag was shaken. The food samples were serially diluted with 0.1% peptone water to yield concentrations that provided counts of colony forming units (cfu) within the counting range of the thin film culture device (approximately 15-100 cfu per device). The thin film devices were inoculated by lifting the transparent film cover sheet, pipetting 1 mL of the diluted sample in the center of the coated bottom film, and replacing the cover sheet. The sample was uniformly spread to the edges of the circular opening by applying downward pressure with a 3M PETRIFILM Flat Spreader. Duplicate thin film culture devices were prepared for each sample. The inoculated devices were incubated at 25° C. for 60 to 72 hours.

The total number of yeast and mold colonies from each sample was counted by visual examination at 48 hours and at the end of the incubation period (60-72 hour timepoint). At each timepoint, the cfu counts of the individual devices were averaged and the average count value was used to calculate the number of colony forming units per milliliter (cfu/mL) in the original undiluted sample. The colonies on reference DRBC plates were counted in the same manner as described for the thin film culture devices. The calculated cfu/mL values for each sample at the 48 hour timepoint are presented in Table 18. The cfu counts for the DRBC reference plates were taken after 5 days of incubation.

TABLE 18

| Food Sample | cfu/mL Using Thin Film Device of Example 11 | cfu/mL Using DRBC Agar (Reference Example) |
|---|---|---|
| Corn kernels | $1.5 \times 10^6$ | $7.8 \times 10^6$ |
| Cut carrots | $8.9 \times 10^6$ | $2.5 \times 10^7$ |
| Tomato paste | $1.8 \times 10^4$ | $2.3 \times 10^3$ |
| Green Chili Puree | $7.5 \times 10^7$ | $7.0 \times 10^7$ |
| Pasta in Meat Sauce | $2.1 \times 10^6$ | $2.5 \times 10^6$ |
| Chicken Seasoning | $6.0 \times 10^3$ | $8.0 \times 10^3$ |

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Various modifications may be made without departing from the spirit and scope of the invention. These and other embodiments are within the scope of the following claims.

The invention claimed is:
1. A culture device, comprising:
a body comprising a self-supporting substrate having a first major surface and a second major surface;
a first adhesive composition disposed on a portion of the first major surface of the substrate;
a substantially dry, cold-water-soluble first hydrogel-forming composition adhered to the first adhesive composition; and
a plurality of indicator agents, the plurality of indicator agents comprising:

5-bromo-4-chloro-3-indolyl acetate, 5-bromo-4-chloro-3-indolyl-beta-D-galactopyranoside, 5-bromo-4-chloro-3-indolyl-beta-D-glucopyranoside, 5-bromo-4-chloro-3-indolyl-alpha-D-glucopyranoside, and 5-bromo-4-chloro-3-indolyl phosphate para-toluidine salt; and a cover sheet attached to the body member, wherein the cover sheet comprises a first major surface facing the body member, and wherein the culture device also comprises a second adhesive composition disposed on a portion of the first major surface of the cover sheet and a substantially dry, cold-water-soluble second hydrogel-forming composition adhered to the second adhesive composition;

wherein at least three of the 5-bromo-4-chloro-3-indolyl acetate, 5-bromo-4-chloro-3-indolyl-beta-D-galactopyranoside, 5-bromo-4-chloro-3-indolyl-beta-D-glucopyranoside, 5-bromo-4-chloro-3-indolyl-alpha-D-glucopyranoside, and 5-bromo-4-chloro-3-indolyl phosphate para-toluidine salt are disposed in the first adhesive composition and/or the second adhesive composition.

2. The culture device of claim 1, wherein the 5-bromo-4-chloro-3-indolyl acetate, 5-bromo-4-chloro-3-indolyl-beta-D-galactopyranoside, 5-bromo-4-chloro-3-indolyl-beta-D-glucopyranoside, 5-bromo-4-chloro-3-indolyl-alpha-D-glucopyranoside, and 5-bromo-4-chloro-3-indolyl phosphate para-toluidine salt are disposed in the first adhesive composition and/or the second adhesive composition.

3. The culture device of claim 1, further comprising a water-insoluble spacer having an aperture, the spacer being attached to the body member or the coversheet and the entire aperture being positioned between the body member and the cover sheet.

4. The culture device of embodiment 21, further comprising a predefined volume of aqueous liquid disposed between the body member and the coversheet, wherein the aqueous liquid and gelling agent form a hydrogel.

5. A method of detecting yeast or mold in a sample, comprising:

contacting a sample and an aqueous liquid with the gelling agent disposed on the first or second adhesive composition of the culture device of claim 1 to form an inoculated culture device;

incubating the inoculated culture device for a period of time; and detecting a yeast or mold colony in the culture device.

6. The method of claim 5, wherein detecting a yeast or mold colony in the culture device comprises detecting in the culture device a presence or an absence of the detectable reporter group of at least one of the indicator agents, wherein detecting the presence of the detectable reporter group is indicative of a presence of a colony of yeast or mold microorganisms.

7. The method of claim 5, wherein contacting a sample with the gelling agent disposed on the first or second adhesive composition of the culture device comprises placing the sample in fluid communication with the at least one nutrient.

8. The method of claim 5, wherein incubating the inoculated culture device comprises incubating the inoculated culture device at a temperature between about 20° C. and about 32° C., inclusive.

9. The method of claim 5, wherein incubating the inoculated culture device for a period of time comprises incubating the inoculated culture device for up to about 72 hours.

10. The method of claim 8, wherein incubating the inoculated culture device for a period of time comprises incubating the inoculated culture device for up to about 60 hours.

11. The method of claim 5, further comprising enumerating yeast or mold colonies present in the inoculated culture device after incubating the inoculated culture device.

* * * * *

UNITED STATES PATENT AND TRADEMARK OFFICE
CERTIFICATE OF CORRECTION

PATENT NO. : 10,640,743 B2
APPLICATION NO. : 15/879582
DATED : May 5, 2020
INVENTOR(S) : Sailaja Chandrapati It is certified that error appears in the above-identified patent and that said Letters Patent is hereby corrected as shown below:

In the Specification

Column 11-12, Line 6, delete "-Methylumbellifelyl-" and insert -- Methylumbelliferyl --

Column 11-12, Line 31, delete "-Nitrophenyl -" and insert -- Nitrophenyl --

Column 13-14, Line 3, delete "-methylumbellifelyl)" and insert -- methylumbelliferyl) --

Column 13-14, Line 4, delete "-methylumbellifelyl)" and insert -- methylumbelliferyl) --

Column 13-14, Line 8, delete "-phophate" and insert -- phosphate --

Column 13-14, Line 40, delete "nanoate" and insert -- nonanoate --

Signed and Sealed this
Sixth Day of July, 2021

Drew Hirshfeld
*Performing the Functions and Duties of the*
*Under Secretary of Commerce for Intellectual Property and*
*Director of the United States Patent and Trademark Office*